United States Patent
Aida et al.

(10) Patent No.: US 11,513,240 B2
(45) Date of Patent: Nov. 29, 2022

(54) RADIATION DETECTION MODULE, RADIATION DETECTOR, AND METHOD FOR MANUFACTURING RADIATION DETECTION MODULE

(71) Applicant: CANON ELECTRON TUBES & DEVICES CO., LTD., Otawara (JP)

(72) Inventors: Hiroshi Aida, Utsunomiya (JP); Hiroshi Horiuchi, Otawara (JP); Masaya Nagai, Utsunomiya (JP)

(73) Assignee: CANON ELECTRON TUBES & DEVICES CO., LTD., Otawara (JP)

( * ) Notice: Subject to any disclaimer, the term of this patent is extended or adjusted under 35 U.S.C. 154(b) by 0 days.

(21) Appl. No.: 17/220,978

(22) Filed: Apr. 2, 2021

(65) Prior Publication Data

US 2021/0247529 A1   Aug. 12, 2021

Related U.S. Application Data

(63) Continuation of application No. PCT/JP2019/044127, filed on Nov. 11, 2019.

(30) Foreign Application Priority Data

Nov. 13, 2018  (JP) .............................. JP2018-213196
Oct. 9, 2019   (JP) .............................. JP2019-185657

(51) Int. Cl.
   *G01T 1/20*     (2006.01)
   *G01T 1/202*    (2006.01)

(52) U.S. Cl.
   CPC .......... *G01T 1/20188* (2020.05); *G01T 1/202* (2013.01); *G01T 1/2006* (2013.01)

(58) Field of Classification Search
   CPC .... G01T 1/2006; G01T 1/202; G01T 1/20188
   See application file for complete search history.

(56) References Cited

U.S. PATENT DOCUMENTS

2003/0001100 A1    1/2003  Dejule
2010/0224784 A1    9/2010  Homma et al.
(Continued)

FOREIGN PATENT DOCUMENTS

JP    2004264231 A  *  9/2004  .............. G01T 1/00
JP    2009-128023 A    6/2009
(Continued)

OTHER PUBLICATIONS

International Search Report dated Feb. 4, 2020 in PCT/JP2019/044127 filed on Nov. 11, 2019, 3 pages

*Primary Examiner* — David P Porta
*Assistant Examiner* — Jeremy S Valentiner
(74) *Attorney, Agent, or Firm* — Oblon, McClelland, Maier & Neustadt, L.L.P.

(57) ABSTRACT

A radiation detection module according to an embodiment includes: an array substrate including multiple photoelectric converters; a scintillator provided on the multiple photoelectric converters; a sealing part that has a frame shape, is provided around the scintillator, is bonded to the array substrate and the scintillator, and includes a thermoplastic resin as a major component; and a moisture-resistant part covering the scintillator from above, in which a peripheral edge vicinity is bonded to an outer surface of the sealing part. The shape of the outer surface of the sealing part is a curved surface protruding outward.

26 Claims, 10 Drawing Sheets

(56) References Cited

U.S. PATENT DOCUMENTS

| | | | |
|---|---|---|---|
| 2011/0147602 A1* | 6/2011 | Ishida | G01T 1/202 |
| | | | 438/57 |
| 2011/0198505 A1 | 8/2011 | Ishida et al. | |
| 2012/0288688 A1 | 11/2012 | Kug et al. | |
| 2019/0113634 A1 | 4/2019 | Jonishi et al. | |

FOREIGN PATENT DOCUMENTS

| | | | | |
|---|---|---|---|---|
| JP | 2011-191290 A | 9/2011 | | |
| JP | 2013-011490 A | 1/2013 | | |
| JP | 2014-081364 A | 5/2014 | | |
| JP | 2015-004560 A | 1/2015 | | |
| JP | 2017-090090 A | 5/2017 | | |
| JP | 2017-111082 A | 6/2017 | | |
| JP | 2017111082 A * | 6/2017 | | G01T 1/20 |
| JP | 2017-181296 A | 10/2017 | | |

* cited by examiner

RADIATION DETECTION MODULE, RADIATION DETECTOR, AND METHOD FOR MANUFACTURING RADIATION DETECTION MODULE

CROSS-REFERENCE TO RELATED APPLICATIONS

This is a continuation application of International Application PCT/JP2019/044127, filed on Nov. 11, 2019. This application also claims priority to Japanese Patent Application No. 2018-213196, filed on Nov. 13, 2018, and No. 2019-185657, filed on Oct. 9, 2019; the entire contents of which are incorporated herein by reference.

FIELD

Embodiments of the invention relate to a radiation detection module, a radiation detector, and a method for manufacturing a radiation detection module.

BACKGROUND

An X-ray detector is an example of a radiation detector. A scintillator that converts X-rays into fluorescence, and an array substrate that converts the fluorescence into an electrical signal are provided in the X-ray detector. There are also cases where a reflective layer is further provided on the scintillator to increase the utilization efficiency of the fluorescence and improve the sensitivity characteristics.

Here, to suppress degradation of characteristics caused by water vapor, etc., it is necessary to isolate the scintillator and the reflective layer from the external atmosphere. For example, when the scintillator includes CsI (cesium iodide): Tl (thallium), CsI:Na (sodium), etc., there is a risk that the characteristic degradation due to water vapor, etc., may increase.

Therefore, technology has been proposed in which, as a structure from which high moisture resistance is obtained, the scintillator and the reflective layer are covered with a hat-shaped moisture-resistant part; and the brim (brim) portion of the moisture-resistant part is bonded to the array substrate.

However, space is necessary for bonding the brim portion to the periphery of the scintillator when the brim portion of the moisture-resistant part is bonded to the array substrate. In recent years, it is desirable to downsize the X-ray detector; however, if the moisture-resistant part has a hat-like shape, there is a risk that downsizing of the X-ray detector can no longer be realized.

Also, when performing a large amount of X-ray irradiation on a human body, the X-ray irradiation amount on the human body is suppressed as much as possible because of the unfavorable effects on health. Therefore, when an X-ray detector is used in medical care, there is a risk that the intensity of the irradiated X-rays may be low, or the intensity of the X-rays passing through the moisture-resistant part may be extremely low. In such a case, the intensity of the transmitted X-rays can be increased if the thickness of the moisture-resistant part is reduced. However, when the thickness of the hat-shaped moisture-resistant part is reduced, cracks, etc., easily occur when molding a foil of aluminum, etc., into a hat-like shape.

Therefore, it is desirable to develop technology in which downsizing of the X-ray detector can be realized, and the thickness of the moisture-resistant part can be reduced.

DETAILED DESCRIPTION

Figure 1:
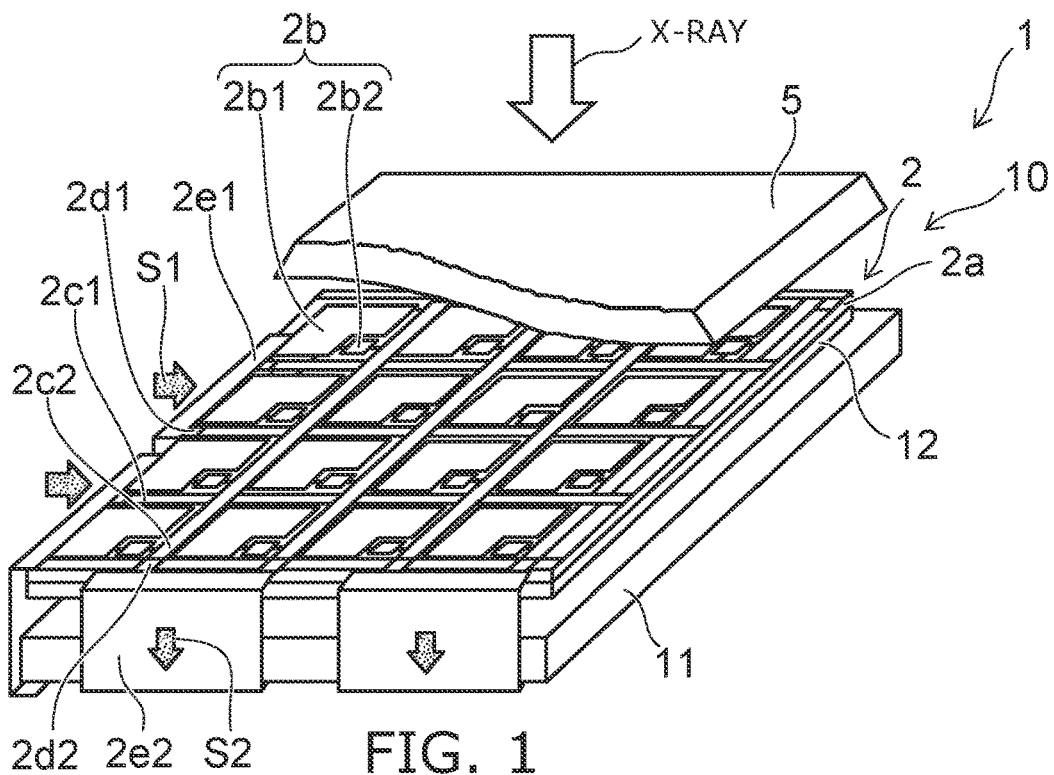
FIG. 1 is a schematic perspective view for illustrating an X-ray detector and an X-ray detection module according to the embodiment.

A radiation detection module according to an embodiment includes: an array substrate including multiple photoelectric converters; a scintillator provided on the multiple photoelectric converters; a sealing part that has a frame shape, is provided around the scintillator, is bonded to the array substrate and the scintillator, and includes a thermoplastic resin as a major component; and a moisture-resistant part covering the scintillator from above, in which a peripheral edge vicinity is bonded to an outer surface of the sealing part. The shape of the outer surface of the sealing part is a curved surface protruding outward.

Embodiments will now be illustrated with reference to the drawings. Similar components in the drawings are marked with the same reference numerals; and a detailed description is omitted as appropriate.

Also, radiation detectors according to embodiments of the invention are applicable to various radiation other than X-rays such as γ-rays, etc. Here, as an example, the case relating to X-rays is described as a typical example of radiation. Accordingly, applications to other radiation as well are possible by replacing "X-ray" with "other radiation" in the embodiments described below.

Also, for example, the radiation detector can be used in general medical care, etc. However, the application of the radiation detector is not limited to general medical care.

(X-Ray Detector and X-Ray Detection Module)

FIG. 1 is a schematic perspective view for illustrating an X-ray detector 1 and an X-ray detection module 10 according to the embodiment.

To avoid complexity, a protective layer 2f, a reflective layer 6, a moisture-resistant part 7, a sealing part 8, etc., are not illustrated in FIG. 1.

Figure 2:
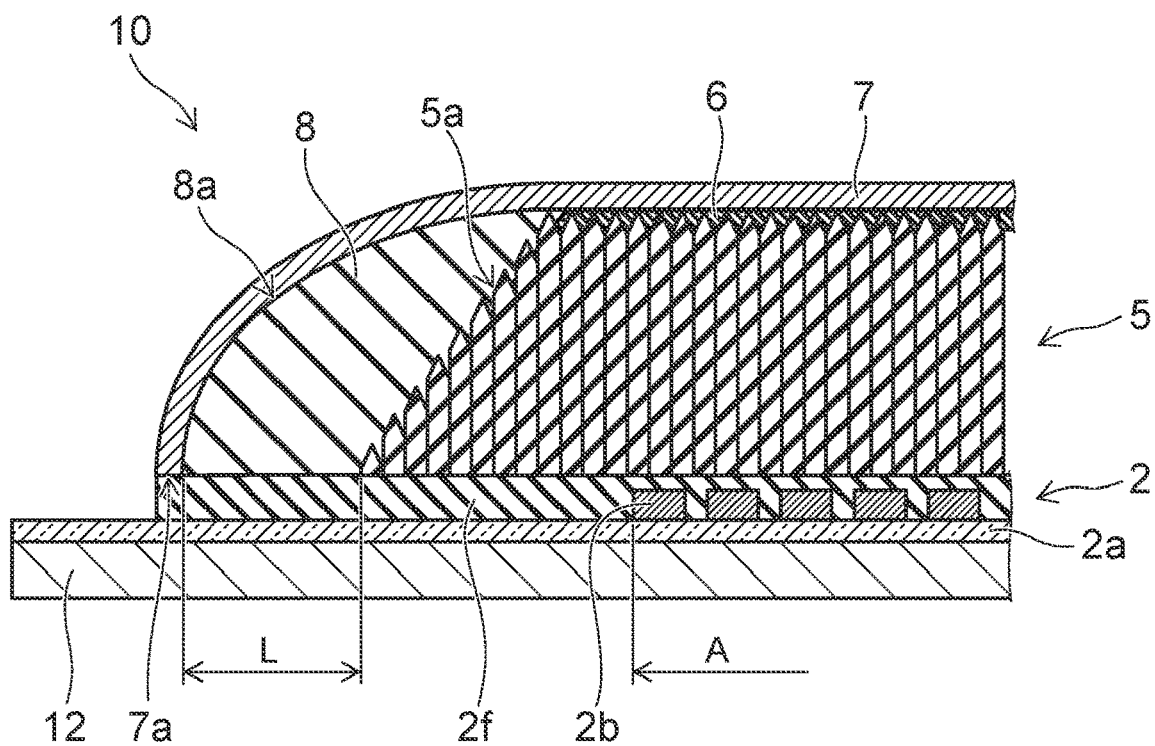
FIG. 2 is a schematic cross-sectional view for illustrating the X-ray detection module.

FIG. 2 is a schematic cross-sectional view for illustrating the X-ray detection module 10.

Figure 3:
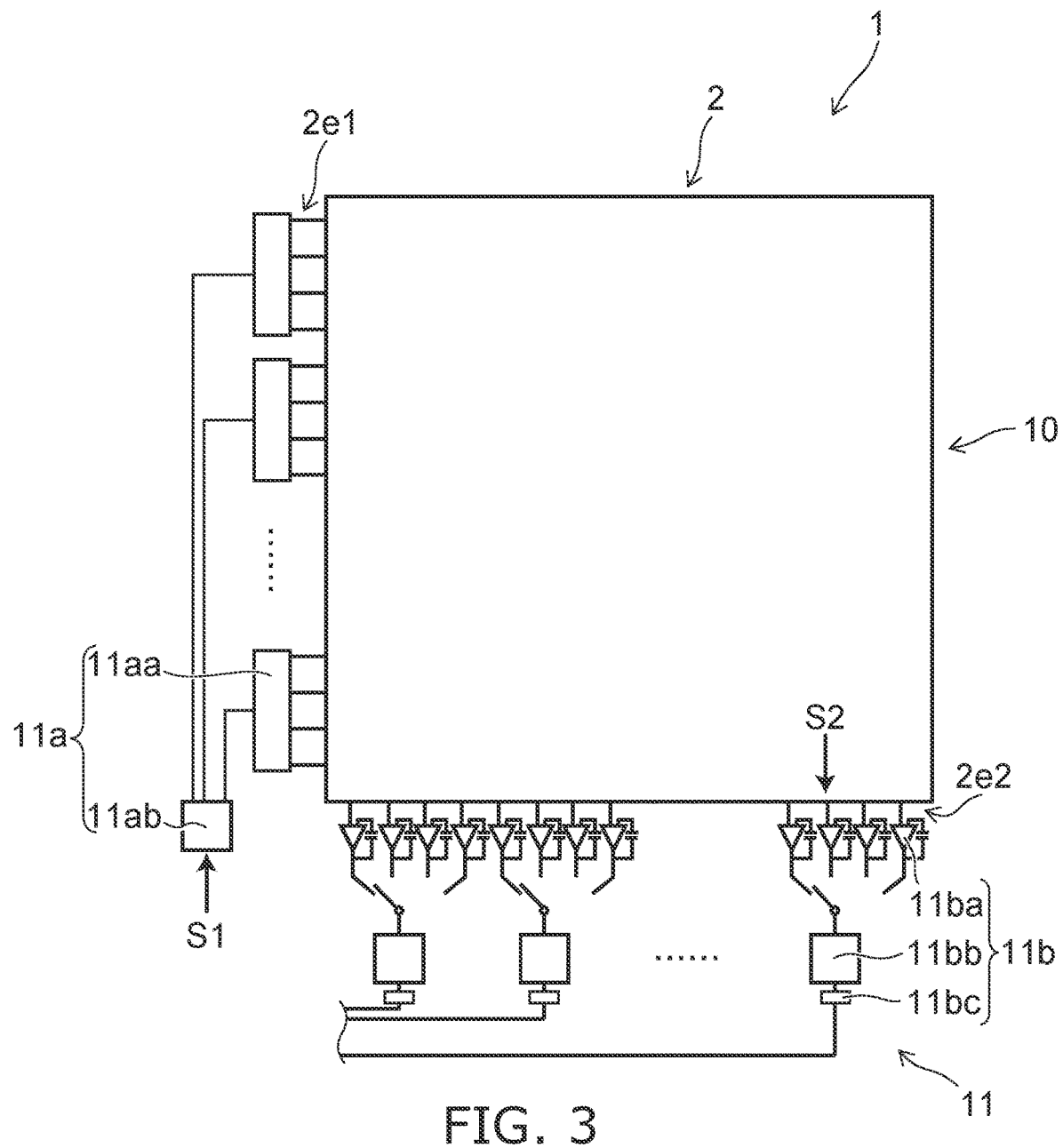
FIG. 3 is a block diagram of the X-ray detector.

FIG. 3 is a block diagram of the X-ray detector 1.

As shown in FIGS. 1 and 2, the X-ray detection module 10 and a circuit board 11 are provided in the X-ray detector 1. Also, a not-illustrated housing can be provided in the X-ray detector 1. The X-ray detection module 10 and the circuit board 11 can be provided inside the housing. For example, a plate-shaped support plate 12 can be provided inside the housing; the X-ray detection module 10 can be located at the surface of the support plate 12 at the incident side of the X-rays; and the circuit board 11 can be located at the surface of the support plate 12 at the side opposite to the incident side of the X-rays.

An array substrate 2, a scintillator 5, the reflective layer 6, the moisture-resistant part 7, and the sealing part 8 are provided in the X-ray detection module 10.

The array substrate 2 includes a substrate 2a, a photoelectric converter 2b, a control line (or gate line) 2c1, a data line (or signal line) 2c2, an interconnect pad 2d1, an interconnect pad 2d2, and the protective layer 2f.

The numbers and the like of the photoelectric converters 2b, the control lines 2c1, and the data lines 2c2 are not limited to those illustrated.

The substrate 2a has a plate shape and is formed from glass such as alkali-free glass, etc. The planar shape of the substrate 2a can be rectangular. The thickness of the substrate 2a can be, for example, about 0.7 mm.

Multiple photoelectric converters 2b are provided at one surface side of the substrate 2a.

The photoelectric converter 2b has a rectangular shape and is provided in a region defined by the control lines 2c1 and the data lines 2c2. The multiple photoelectric converters 2b are arranged in a matrix configuration. One photoelectric converter 2b corresponds to one pixel (pixel) of an X-ray image.

A photoelectric conversion element 2b1 and a thin film transistor (TFT; Thin Film Transistor) 2b2 that is a switching element are provided in each of the multiple photoelectric converters 2b.

Also, a not-illustrated storage capacitor that stores a signal charge converted by the photoelectric conversion element 2b1 can be provided. For example, the storage capacitor has a rectangular flat plate shape and can be provided under each thin film transistor 2b2. However, photoelectric conversion element 2b1 also can be used as the storage capacitor according to the capacitance of the photoelectric conversion element 2b1.

The photoelectric conversion element 2b1 can be, for example, a photodiode, etc.

The thin film transistor 2b2 switches between storing and discharging the charge to and from the storage capacitor. The thin film transistor 2b2 includes a gate electrode, a drain electrode, and a source electrode. The gate electrode of the thin film transistor 2b2 is electrically connected with the corresponding control line 2c1. The drain electrode of the thin film transistor 2b2 is electrically connected with correspond data line 2c2. The source electrode of the thin film transistor 2b2 is electrically connected to the corresponding photoelectric conversion element 2b1 and storage capacitor. Also, the storage capacitor and the anode side of the photoelectric conversion element 2b1 can be connected to ground. Also, the storage capacitor and the anode side of the photoelectric conversion element 2b1 can be connected to a not-illustrated bias line.

Multiple control lines 2c1 are provided to be parallel to each other with a prescribed spacing interposed. For example, the control line 2c1 extends in a row direction. One control line 2c1 is electrically connected with one of the multiple interconnect pads 2d1 provided at the peripheral edge vicinity of the substrate 2a. One of multiple interconnects provided in a flexible printed circuit board 2e1 is electrically connected to one interconnect pad 2d1. The other ends of the multiple interconnects provided in the flexible printed circuit board 2e1 are electrically connected respectively to read circuits 11a provided in the circuit board 11.

Multiple data lines 2c2 are provided to be parallel to each other with a prescribed spacing interposed. For example, the data line 2c2 extends in a column direction orthogonal to the row direction. One data line 2c2 is electrically connected with one of the multiple interconnect pads 2d2 provided at the peripheral edge vicinity of the substrate 2a. One of multiple interconnects provided in a flexible printed circuit board 2e2 is electrically connected to one interconnect pad 2d2. The other ends of the multiple interconnects provided in the flexible printed circuit board 2e2 are electrically connected respectively to signal detection circuits 11b provided in the circuit board 11.

For example, the control line 2c1 and the data line 2c2 can be formed using a low-resistance metal such as aluminum, chrome, etc.

The protective layer 2f covers the photoelectric converter 2b, the control line 2c1, and the data line 2c2. The protective layer 2f can be formed from an insulating material. The insulating material can be, for example, an oxide insulating material, a nitride insulating material, an oxynitride insulating material, a resin, etc.

The scintillator 5 is located on the multiple photoelectric converters 2b and converts the incident X-rays into visible light, i.e., fluorescence. The scintillator 5 is provided to cover a region (an effective pixel region A) on the substrate 2a in which the multiple photoelectric converters 2b are provided.

The scintillator 5 can include, for example, cesium iodide (CsI):thallium (Tl), sodium iodide (NaI):thallium (Tl), cesium bromide (CsBr):europium (Eu), etc. The scintillator 5 can be formed using vacuum vapor deposition. If the scintillator 5 is formed using vacuum vapor deposition, a scintillator 5 that is made of an aggregate of multiple columnar crystals is formed. The thickness of the scintillator 5 can be, for example, about 600 μm.

A mask that has an opening is used when forming the scintillator 5 by using vacuum vapor deposition. In such a case, the scintillator 5 is formed in a position facing the opening on the array substrate 2 (on the effective pixel region A). Also, a film that is formed by vapor deposition is formed on the surface of the mask. Then, at the vicinity of the opening of the mask, the film grows to gradually jut into the opening. When the film juts into the opening, the vapor deposition of the array substrate 2 is suppressed at the vicinity of the opening. Therefore, as shown in FIGS. 1 and 2, the thickness of the peripheral edge vicinity of the scintillator 5 gradually decreases outward.

Also, for example, the scintillator 5 can be formed using terbium-activated sulfated gadolinium ($Gd_2O_2S$/Tb or GOS), etc. In such a case, a trench portion that has a matrix configuration can be provided so that a rectangular-prism-shaped scintillator 5 is provided for each of the multiple photoelectric converters 2b.

The reflective layer 6 is provided to increase the utilization efficiency of the fluorescence and improve the sensitivity characteristics. In other words, the reflective layer reflects the light of the fluorescence generated by the scintillator 5 and oriented toward the side opposite to the side at which the photoelectric converter 2b is provided, and causes the light to be oriented toward the photoelectric converter 2b. However, the reflective layer 6 is not always necessary; it is sufficient to provide the reflective layer 6 according to the necessary sensitivity characteristics of the X-ray detection module 10, etc.

A case where the reflective layer 6 is provided will now be described as an example.

The reflective layer 6 is provided at the incident side of the X-rays of the scintillator 5. The reflective layer 6 covers at least the upper surface of the scintillator 5. The reflective layer 6 also can cover a side surface 5a of the scintillator 5. For example, the reflective layer 6 can be formed by coating, on the scintillator 5, a material in which a solvent, a resin, and light-scattering particles made of titanium oxide ($TiO_2$), etc., are mixed, and by drying the coating.

Also, for example, the reflective layer 6 can be formed by forming, on the scintillator 5, a layer made of a metal having high light reflectance such as a silver alloy, aluminum, etc.

Also, for example, the reflective layer 6 can be made by providing, on the scintillator 5, a sheet having a surface made of a metal having high light reflectance such as a silver alloy, aluminum, and the like, a resin sheet including light-scattering particles, etc.

When a paste-like material is coated onto the scintillator and dried, there are cases where the scintillator 5 delaminates from the array substrate 2 because the scintillator 5 is pulled by the contraction of the material when drying. Therefore, it is favorable for a sheet-like reflective layer 6 to be provided on the scintillator 5. In such a case, although the sheet-like reflective layer 6 also can be bonded onto the scintillator 5 by using, for example, double-sided tape, etc., it is favorable for the sheet-like reflective layer 6 to be placed on the scintillator 5. If the sheet-like reflective layer 6 is placed on the scintillator 5, it is easy to suppress the delamination of the scintillator 5 from the array substrate 2 caused by the expansion or contraction of the reflective layer 6.

The moisture-resistant part 7 is provided to suppress degradation of the characteristics of the reflective layer 6 and the characteristics of the scintillator 5 due to moisture included in the air.

The moisture-resistant part 7 covers the scintillator 5 and at least a portion of the sealing part 8. A gap may be between the moisture-resistant part 7, the reflective layer 6, etc.; or the moisture-resistant part 7, the reflective layer 6, etc., may be in contact. For example, if the moisture-resistant part and the sealing part 8 are bonded in an environment depressurized from atmospheric pressure, the moisture-resistant part 7, the reflective layer 6, etc., can be in contact. Also, generally, voids of about 10% to 40% of the volume of the scintillator 5 exist in the scintillator 5. Therefore, when a gas is included in the voids, there is a risk that the moisture-resistant part 7 may be damaged by the expansion of the gas when the X-ray detector 1 is transported by an aircraft, etc. If the moisture-resistant part 7 and the sealing part 8 are bonded in an environment depressurized from atmospheric pressure, the damage of the moisture-resistant part 7 can be suppressed even when the X-ray detector 1 is transported by an aircraft, etc. In other words, it is favorable for the pressure of the space defined by the sealing part 8 and the moisture-resistant part 7 to be less than atmospheric pressure.

Here, there are cases where bubbles and/or voids are inside the sealing part 8, gaps and/or leakage paths are between the sealing part 8 and the moisture-resistant part 7, or gaps and/or leakage paths are between the sealing part 8 and the array substrate 2. In such a case, when the moisture-resistant part 7 and the sealing part 8 are bonded in an environment depressurized from atmospheric pressure and subsequently returned to an atmospheric pressure environment, ambient air may penetrate the interior via the gaps and/or leakage paths, etc. When ambient air penetrates the interior, the moisture-resistant part 7 and the scintillator 5 are not closely adhered; wrinkles occur in the surface of the moisture-resistant part 7; and the tension is lost. Therefore, the existence of gaps and/or leakage paths, etc., can be easily known by using the naked eye. Although there is a risk that the life of a product in which gaps and/or leakage paths, etc., exist may be reduced, such a product can be easily detected and removed in the inspection. Therefore, it is easy to improve the quality of the X-ray detector 1.

The moisture-resistant part 7 can be a sheet including a metal. The metal can be, for example, a metal including aluminum, a metal including copper, a metal including magnesium, a metal including tungsten, stainless steel, a Kovar material, etc. In such a case, if the moisture-resistant part 7 includes a metal, the moisture that passes through the moisture-resistant part 7 can be substantially completely eliminated.

Also, the moisture-resistant part 7 can be a stacked sheet in which a resin film and a metal film are stacked. In such a case, for example, the resin film can be formed from a polyimide resin, an epoxy resin, a polyethylene terephthalate resin, Teflon (registered trademark), low density polyethylene, high density polyethylene, elastic rubber, etc. For example, the metal film can include the metals described above. For example, the metal film can be formed using sputtering, laminating, etc. In such a case, it is favorable for the metal film to be provided at the scintillator 5 side. Thus, scratches of the metal film due to an external force, etc., can be suppressed because the metal film can be covered with the resin film. Also, if the metal film is provided further on the inner side (the scintillator 5 side) than the resin film, the degradation of the characteristics of the scintillator 5 due to moisture permeability via the resin layer can be suppressed.

Also, the inorganic film can be provided with the metal film or instead of the metal film. The inorganic film can be, for example, a film that includes silicon oxide, aluminum oxide, etc. For example, the inorganic film can be formed using sputtering, etc.

When a stacked sheet including a metal film is used, for example, a resin film that has substantially the same thickness as the thickness of the metal film can be used. If a resin film having such a thickness is provided, the occurrence of pinholes in the moisture-resistant part 7 in the manufacturing processes can be suppressed because the rigidity of the moisture-resistant part 7 can be increased. Generally, the linear expansion coefficient of a resin is greater than the linear expansion coefficient of a metal; therefore, warp of the array substrate 2 described below easily occurs when the thickness of the resin film is too thick. Therefore, it is favorable for the thickness of the resin film to be not more than the thickness of the metal film.

Also, the thickness of the moisture-resistant part 7 can be determined by considering the absorption of the X-rays, the rigidity, etc. In such a case, when the thickness of the moisture-resistant part 7 is increased, the amount of the X-rays absorbed by the moisture-resistant part 7 is increased. On the other hand, when the thickness of the moisture-resistant part 7 is reduced, the rigidity is reduced; and damage occurs more easily.

For example, when the thickness of the moisture-resistant part 7 is less than 10 μm, there is a risk that the rigidity of the moisture-resistant part 7 may become too low; pinholes may occur due to damage due to an external force, etc.; and leakage may occur. When the thickness of the moisture-resistant part 7 is greater than 50 μm, the rigidity of the moisture-resistant part 7 becomes too high, and the conformity to the unevenness of the upper end of the scintillator 5 is poor. Therefore, there is a risk that it is difficult to check the gaps and/or leakage paths described above. Moreover, there is a risk that warp of the array substrate 2 described below may easily occur.

Therefore, it is favorable for the thickness of the moisture-resistant part 7 to be not less than 10 μm and not more than 50 μm.

In such a case, the moisture-resistant part 7 can be, for example, an aluminum foil having a thickness not less than 10 μm and not more than 50 μm. If the thickness of the aluminum foil is not less than 10 μm and not more than 50 μm, the transmitted amount of the X-rays can be about 20% to 30% greater compared to an aluminum foil having a thickness of 100 μm. Also, if the aluminum foil has a thickness not less than 10 μm and not more than 50 μm, the occurrence of the leakage described above can be suppressed, and the check of the gaps and/or leakage paths described above is easy. Also, the warp of the array substrate 2 described below can be suppressed.

Here, when a large amount of X-ray irradiation on the human body is performed, the X-ray irradiation amount on the human body is suppressed as much as possible because of the unfavorable effects on health. Therefore, when the X-ray detector 1 is used in medical care, there is a risk that the intensity of the irradiated X-rays may be low, and the intensity of the X-rays that pass through the moisture-resistant part 7 may be extremely low. The moisture-resistant part 7 according to the embodiment is a sheet having a thickness not less than 10 μm and not more than 50 μm; therefore, the imaging of the X-ray image is possible even when the intensity of the irradiated X-rays is low.

In such a case, the rigidity of the moisture-resistant part 7 is reduced when the thickness of the moisture-resistant part 7 is reduced. Therefore, when a stereoscopic moisture-resistant part is made by providing a brim portion, etc., for example, cracks, etc., easily occur when pressing the metal foil. As shown in FIG. 2, the peripheral edge vicinity of the moisture-resistant part 7 having the sheet configuration is bonded to an outer surface 8a of the sealing part 8. Therefore, it is unnecessary to pre-pattern the moisture-resistant part 7 into a three-dimensional configuration; and the moisture-resistant part 7 that has a sheet configuration can be bonded to the outer surface 8a of the sealing part 8 as-is. As a result, even when the thickness of the moisture-resistant part 7 is not less than 10 μm and not more than 50 μm, the occurrence of cracks, etc., in the moisture-resistant part 7 can be suppressed.

Also, as described below, the sealing part 8 and the peripheral edge vicinity of the moisture-resistant part 7 are bonded by heating the peripheral edge vicinity of the moisture-resistant part 7. In such a case, thermal stress is generated between the sealing part 8 and the peripheral edge vicinity of the moisture-resistant part 7 when reducing the temperature of the peripheral edge vicinity of the moisture-resistant part 7 and the temperature of the sealing part 8. When the thermal stress is generated between the sealing part 8 and the peripheral edge vicinity of the moisture-resistant part 7, there is a risk that delamination may occur between the sealing part 8 and the peripheral edge vicinity of the moisture-resistant part 7. When delamination occurs, there is a risk that the moisture resistance may markedly decrease. Because the thickness of the moisture-resistant part 7 is set to be not less than 10 μm and not more than 50 μm, the moisture-resistant part 7 easily elongates when the thermal stress is generated. Therefore, the occurrence of the delamination between the sealing part 8 and the peripheral edge vicinity of the moisture-resistant part 7 can be suppressed because the thermal stress can be relaxed.

As shown in FIG. 2, the sealing part 8 is bonded to the array substrate 2 and the side surface 5a of the scintillator 5. In such a case, the sealing part 8 can be closely adhered with the side surface 5a of the scintillator 5. When the scintillator 5 is an aggregate of multiple columnar crystals, an unevenness is formed in the side surface 5a of the scintillator 5. Therefore, if a portion of the sealing part 8 is provided inside the unevenness of the side surface 5a of the scintillator 5, the bonding strength between the sealing part 8 and the scintillator 5 can be increased. The sealing part 8 can be closely adhered with the array substrate 2. If the sealing part 8 and the array substrate 2 are closely adhered, the moisture that is included in ambient air, etc., can be prevented from passing between the sealing part 8 and the array substrate 2 and reaching the scintillator 5.

The shape of the outer surface 8a of the sealing part 8 can be a curved surface protruding outward. Thus, a distance L between the outer surface 8a of the sealing part 8 and the side surface 5a of the scintillator 5 can be lengthened. Therefore, the moisture included in ambient air, etc., can be prevented from passing through the interior of the sealing part 8 and reaching the scintillator 5.

Also, if the shape of the outer surface 8a of the sealing part 8 is a curved surface protruding outward, it is easy for the peripheral edge vicinity of the moisture-resistant part 7 to conform to the outer surface 8a of the sealing part 8. Therefore, it is easy to closely adhere the moisture-resistant part 7 to the sealing part 8. Also, because the moisture-resistant part 7 can be smoothly deformed, the occurrence of cracks, etc., in the moisture-resistant part 7 can be suppressed even when the thickness of the moisture-resistant part 7 is reduced.

Also, as shown in FIG. 2, when the moisture-resistant part 7 is closely adhered to the sealing part 8, it is favorable for a peripheral end surface 7a of the moisture-resistant part 7 to contact the array substrate 2, or for the peripheral end surface 7a to be positioned at the vicinity of the array substrate 2. Thus, the penetration of the moisture included in ambient air, etc., into the sealing part 8 can be effectively suppressed.

Also, it is favorable for the height of the sealing part 8 to be not more than the height of the scintillator 5. If the height of the sealing part 8 is not more than the height of the scintillator 5, the sheet that is used to form the moisture-resistant part 7 can be deformed without excessive force; therefore, the occurrence of wrinkles, rupture, pinholes, etc., in the moisture-resistant part 7 can be suppressed.

Furthermore, if the height of the sealing part 8 is less than the height of the scintillator 5, the peripheral edge vicinity of the moisture-resistant part 7 can sag. As long as the peripheral edge vicinity of the moisture-resistant part 7 can sag, the difference between the thermal shrinkage of the moisture-resistant part 7 and the thermal shrinkage of the array substrate 2 can be absorbed. Therefore, the deformation of the array substrate 2 due to the thermal stress can be suppressed.

Details relating to the height of the sealing part 8 being set to be less than the height of the scintillator 5 are described below (referring to FIG. 8).

The sealing part 8 can include a thermoplastic resin as a major component. If the sealing part 8 includes a thermoplastic resin as a major component, the array substrate 2, the scintillator 5, and the moisture-resistant part 7 can be bonded by heating. Here, for example, if the sealing part 8 includes an ultraviolet-curing resin as the major component, it is necessary to irradiate ultraviolet light when bonding the sealing part 8 with the array substrate 2, the scintillator 5, and the moisture-resistant part 7. However, the ultraviolet light cannot be transmitted because the moisture-resistant part 7 includes a metal, etc. Also, when the moisture-resistant part 7 is such that the moisture-resistant part 7 transmits ultraviolet light, there is a risk that the scintillator 5 may be discolored by the ultraviolet light; and the fluorescence that is generated may be absorbed.

Conversely, because the sealing part 8 includes a thermoplastic resin as a major component, the bonding can be more easily performed by heating. Also, the scintillator 5 is not discolored by the ultraviolet light. Also, the time necessary to heat and cool the sealing part 8 can be short; therefore, a reduction of the manufacturing time and even a reduction of the manufacturing cost can be realized.

The thermoplastic resin can be, for example, nylon, PET (Polyethyleneterephthalate), polyurethane, polyester, polyvinyl chloride, ABS (Acrylonitrile Butadiene Styrene), acrylic, polystyrene, polyethylene, polypropylene, etc. In such a case, the water vapor permeability coefficient of polyethylene is 0.068 g·mm/day·m$^2$, and the water vapor permeability coefficient of polypropylene is 0.04 g·mm/day·m$^2$. Therefore, if the sealing part 8 includes at least one of polyethylene or polypropylene as a major component, the moisture that reaches the scintillator 5 by passing through the sealing part 8 can be drastically reduced.

The rigidity of the thermoplastic resin can be less than the rigidity of the moisture-resistant part 7.

Also, the sealing part 8 can further include a filler that includes an inorganic material. If a filler that is made of an inorganic material is included in the sealing part 8, the permeation of the moisture can be further suppressed. The inorganic material can be, for example, talc, graphite, mica, kaolin (clay including kaolinite as a major component), etc. For example, the filler can be a filler that has a flattened form. The diffusion of the moisture that penetrates the interior of the sealing part 8 from the outside is impeded by the filler made of the inorganic material; therefore, the rate of the moisture passing through the sealing part 8 can be reduced. Therefore, the amount of the moisture reaching the scintillator 5 can be reduced.

Here, there are cases where the X-ray detector 1 that is stored in a high temperature and humidity environment is used in an environment having a lower temperature. In such a case, there are cases where the water vapor that is inside the housing condenses and adheres to the surface of the X-ray detector 1. When there are fine cracks in the outer surface 8*a* of the sealing part 8, there is a risk that the moisture adhered to the surface may penetrate the cracks and be guided into the sealing part 8. Also, there are cases where the X-ray detector 1 is transferred in an environment that is below the freezing point, and the moisture that has penetrated the cracks freezes. When the moisture that has penetrated the cracks freezes, the volume increases; therefore, the cracks become large, and the moisture easily penetrates further. When this is repeated, there is a risk that damage of the sealing part 8, delamination of the moisture-resistant part 7 and the sealing part 8, delamination of the array substrate 2 and the sealing part 8, etc., may occur.

Therefore, it is favorable for at least the outer surface 8*a* of the sealing part 8 to be water-repellent. If at least the outer surface 8*a* of the sealing part 8 is water-repellent, the penetration of the moisture into the cracks can be suppressed.

For example, a water repellent can be coated onto the outer surface 8*a* of the sealing part 8. Also, the outer surface 8*a* can be water-repellent if the sealing part 8 includes at least one of polyethylene or polypropylene as a major component.

Also, it is favorable to check the existence or absence of bubbles, foreign matter, leakage paths, etc., by observing the interior directly after coating the thermoplastic resin in a frame shape. The production efficiency can be increased as long as such a check can be performed using the naked eye or an optical microscope. Therefore, it is favorable for the thermoplastic resin that is coated in the frame shape to be transparent even at the portion where the thickness is thickest. In other words, it is favorable for the sealing part 8 to be transmissive. Thus, the products that have bubbles, foreign matter, leakage paths, etc., and have a risk of a shorter life can be easily removed. Therefore, the quality of the product can be improved.

Returning to FIG. 1, the circuit board 11 will now be described.

As shown in FIG. 1, the circuit board 11 is located at the side opposite to the side of the array substrate 2 where the scintillator 5 is located. The circuit board 11 is electrically connected with the X-ray detection module 10 (the array substrate 2).

As shown in FIG. 3, the read circuit 11*a* and the signal detection circuit 11*b* are provided in the circuit board 11. These circuits can be provided in one substrate; or these circuits can be separated and provided in multiple substrates.

The read circuit 11*a* switches between the on-state and the off-state of the thin film transistor 2*b*2.

The read circuit 11*a* includes multiple gate drivers 11*aa* and a row selection circuit 11*ab*.

A control signal S1 is input to the row selection circuit 11*ab* from a not-illustrated image processor, etc., provided outside the X-ray detector 1. The row selection circuit 11*ab* inputs the control signal S1 to the corresponding gate driver 11*aa* according to the scanning direction of the X-ray image.

The gate driver 11*aa* inputs the control signal S1 to the corresponding control line 2*c*1.

For example, the read circuit 11*a* sequentially inputs the control signal S1 via the flexible printed circuit board 2*e*1 to each control line 2*c*1. The thin film transistor 2*b*2 is set to the on-state by the control signal S1 input to the control line 2*c*1; and a charge (an image data signal S2) from a storage capacitor can be received.

The signal detection circuit 11*b* includes multiple integrating amplifiers 11*ba*, multiple selection circuits 11*bb*, and multiple AD converters 11*bc*.

One integrating amplifier 11*ba* is electrically connected with one data line 2*c*2. The integrating amplifier 11*ba* sequentially receives the image data signals S2 from the photoelectric converters 2b. Then, the integrating amplifier 11ba integrates the current flowing within a constant amount of time and outputs a voltage corresponding to the integral to the selection circuit 11bb. Thus, it is possible to convert, into a voltage value, the value (the charge amount) of the current flowing through the data line 2c2 within a prescribed period of time. In other words, the integrating amplifier 11ba converts, to potential information, image data information that corresponds to the intensity distribution of the fluorescence generated by the scintillator 5.

The selection circuit 11bb selects the integrating amplifier 11ba that performs the reading, and sequentially reads the image data signal S2 converted into the potential information.

The AD converter 11bc sequentially converts the image data signal S2 that is read into a digital signal. The image data signal S2 that is converted into the digital signal is input to an image processor via an interconnect. The image data signal S2 that is converted into the digital signal may be transmitted to the image processor by a wireless technique.

The image processor forms an X-ray image based on the image data signal S2 converted into the digital signal. Also, the image processor can be integrated with the circuit board 11.

X-ray detection modules according to other embodiments will now be described.

Figure 4A:
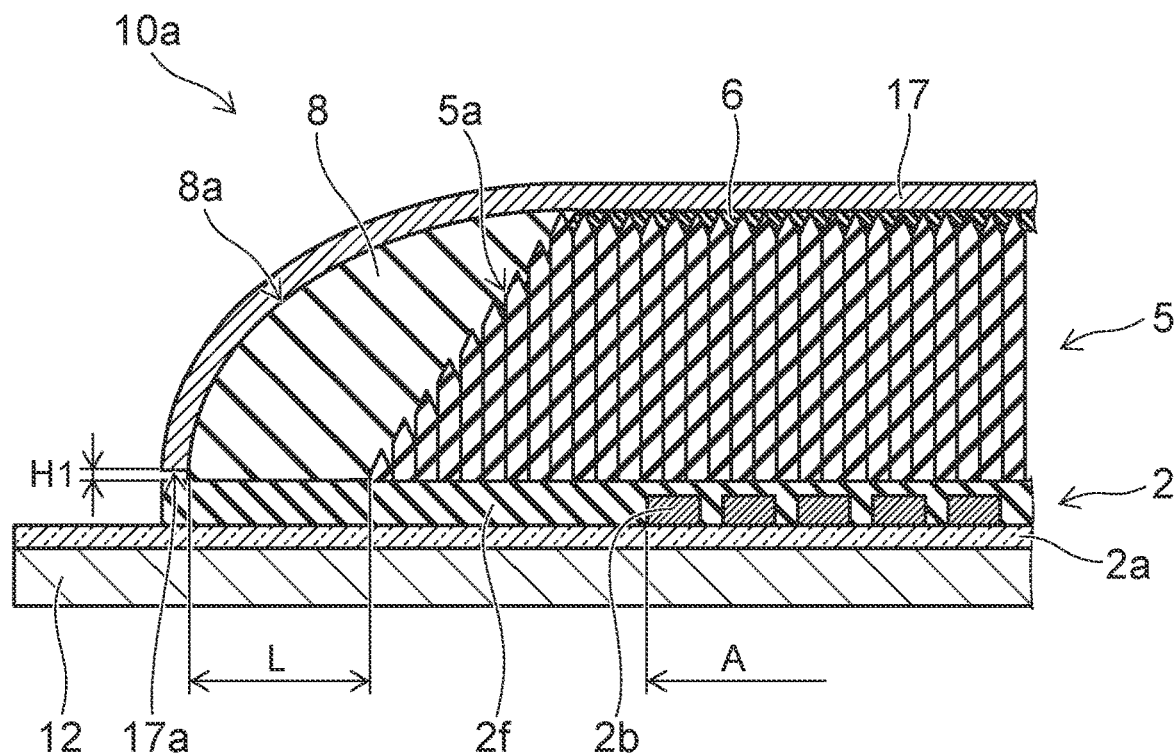
FIGS. 4A and 4B are schematic cross-sectional views for illustrating an X-ray detection module according to another embodiment.
Figure 4B:
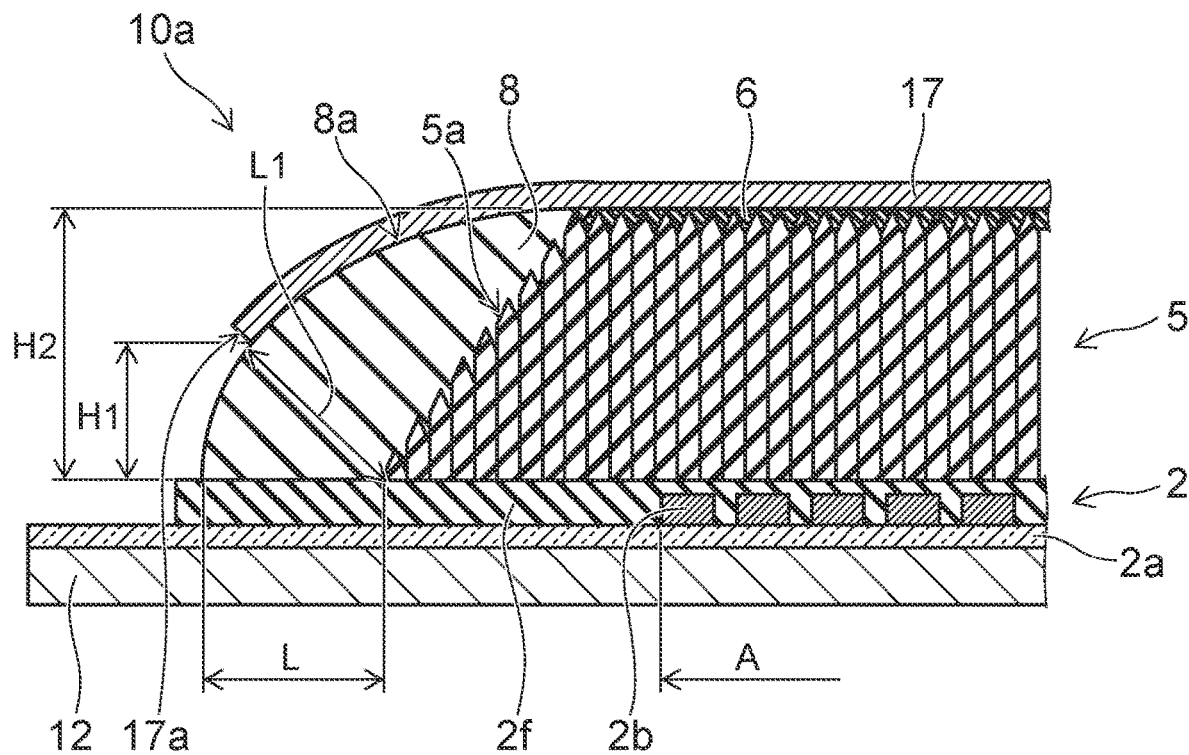

FIGS. 4A and 4B are schematic cross-sectional views for illustrating an X-ray detection module 10a according to another embodiment.

As described below, the sealing part 8 is formed by coating a softened thermoplastic resin in a frame shape on the array substrate 2, or by providing a thermoplastic resin in a frame shape on the array substrate 2 by using a 3D printer, etc. Therefore, there are cases where the dimension of the sealing part 8 fluctuates.

When the dimension of the sealing part 8 fluctuates, there are cases where the peripheral end surface 7a of the moisture-resistant part 7 interferes with the array substrate 2, and wrinkles, etc., occur at the peripheral edge vicinity of the moisture-resistant part 7. When wrinkles, etc., occur at the peripheral edge vicinity of the moisture-resistant part 7, there is a risk that delamination of the moisture-resistant part 7, etc., may occur.

In such a case, as shown in FIG. 4A, a distance H1 can be provided between the array substrate 2 and a peripheral end surface 17a of a moisture-resistant part 17. For example, it is sufficient to set the dimension of the moisture-resistant part 17 having the sheet configuration to be short. Thus, even if the dimension of the sealing part 8 fluctuates, the occurrence of wrinkles, etc., at the peripheral edge vicinity of the moisture-resistant part 17 can be suppressed.

In such a case, when the distance H1 is too large, there is a risk that much moisture may penetrate into the sealing part 8. According to knowledge obtained by the inventors, as shown in FIG. 4B, it is favorable for the distance H1 to be not more than one-half of a height H2 of the sealing part 8. In such a case, the penetration of the moisture into the sealing part 8 is reduced if the distance H1 is reduced.

Figure 5:
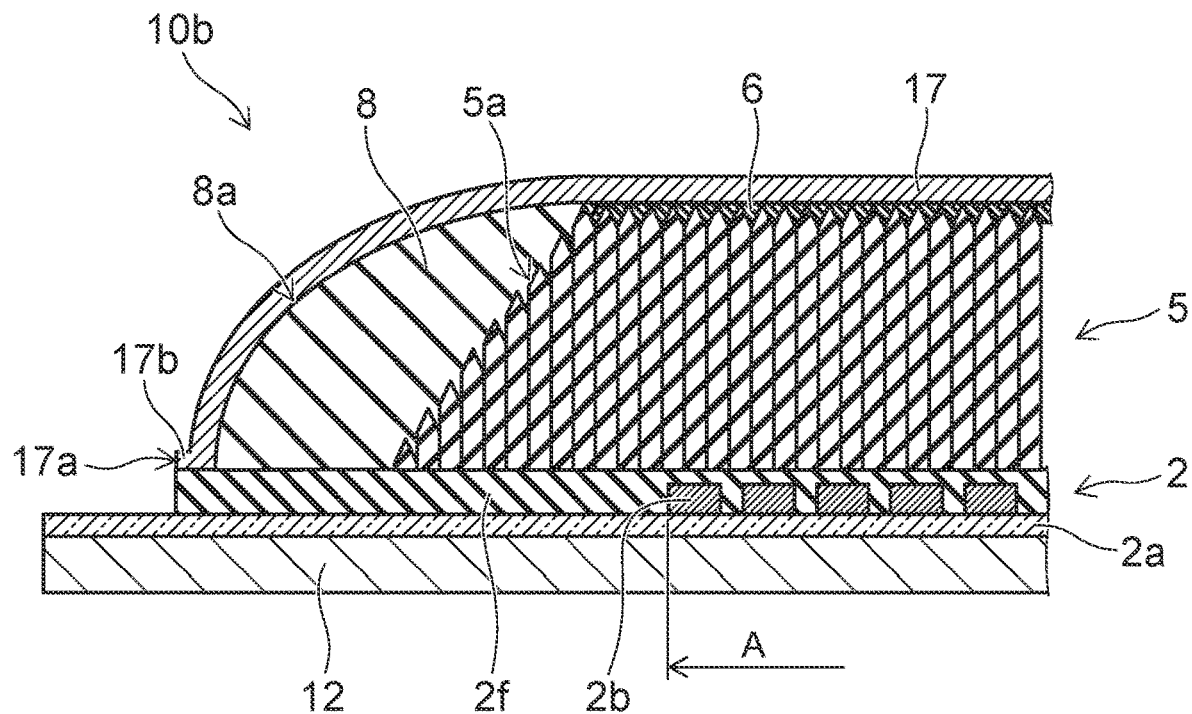
FIG. 5 is a schematic cross-sectional view for illustrating an X-ray detection module according to another embodiment.

FIG. 5 is a schematic cross-sectional view for illustrating an X-ray detection module 10b according to another embodiment.

Figure 6A:
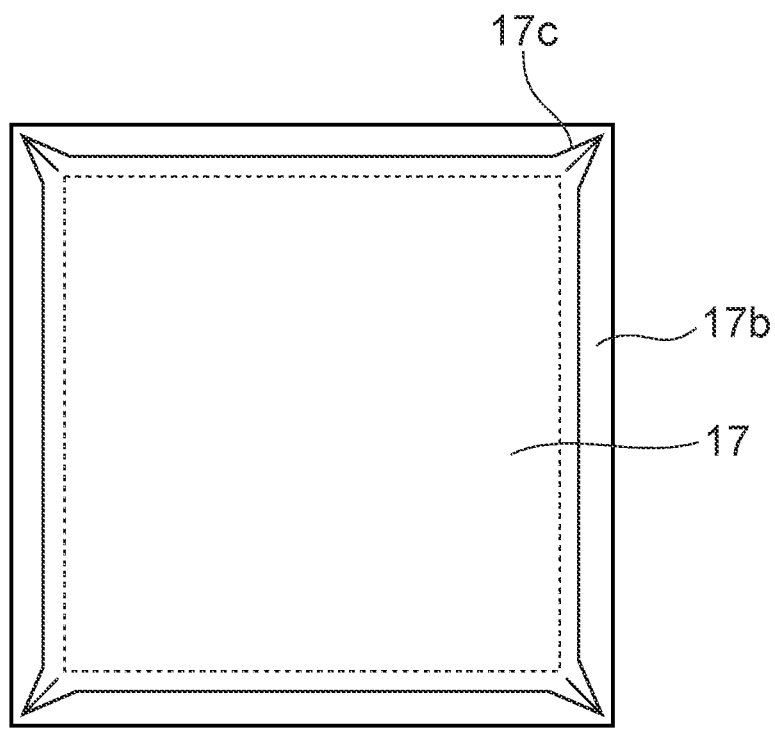
FIG. 6A is a schematic plan view of a moisture-resistant part.

FIG. 6A is a schematic plan view of the moisture-resistant part 17.

Figure 6B:
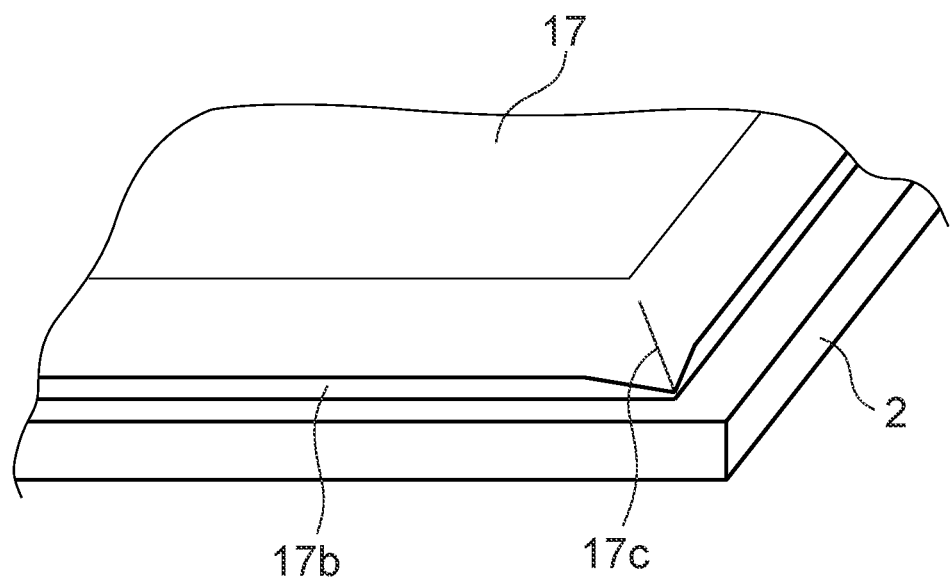
FIG. 6B is a schematic perspective view of the moisture-resistant part 17.

FIG. 6B is a schematic perspective view of the moisture-resistant part 17.

As shown in FIG. 5, the peripheral edge vicinity of the moisture-resistant part 17 can be bent along the array substrate 2 as well. In other words, a bent portion 17b that is along the array substrate 2 can be provided in the peripheral edge of the moisture-resistant part 17. In such a case, the bent portion 17b also can be bonded to the array substrate 2. Thus, the outer surface 8a of the sealing part 8 can be covered with the moisture-resistant part 17; therefore, the penetration of the moisture into the moisture-resistant part 17 can be effectively suppressed. When the dimension of the bent portion 17b is too large, there is a risk that downsizing of the X-ray detection module 10b, and even downsizing of the X-ray detector 1, cannot be realized. Therefore, it is favorable for the dimension of the bent portion 17b to be, for example, not more than 2 mm.

Also, the following problem occurs when the peripheral edge vicinity of the moisture-resistant part 17 is bent.

The moisture-resistant part 17 can be formed using a sheet that has no distortion or unevenness. When the sheet that is used to form the moisture-resistant part 17 is used to cover the scintillator 5, the sheet is in a lifted state separated from the array substrate 2 by the amount of the thickness of the scintillator 5. It is easy to bend the peripheral edge vicinity of the sheet in such a state along the sealing part 8 toward the array substrate 2 side; and stretching stress is substantially not applied to the sheet.

However, it is geometrically impossible to bend the sheet at the portions of the corners of the sealing part 8 having a frame shape into the same shape as at the sides. Therefore, it is necessary to stretch a portion of the sheet to be along the sealing part 8.

It is necessary for the moisture-resistant part 17 to have a function of shielding the moisture from the outside; however, when a portion of the sheet is stretched, there is a risk that the portion may become thin, fine cracks may occur, and pinholes may occur. When cracks and/or pinholes occur, the capability of shielding the moisture decreases.

In such a case, if a convex protrusion 17c that protrudes outward is provided at the corner portion of the moisture-resistant part 17 as shown in FIGS. 6A and 6B, the geometric distortion described above can be absorbed. Therefore, the stretching of the portion of the sheet can be suppressed; therefore, the occurrence of the cracks and/or the pinholes can be suppressed.

Figure 7:
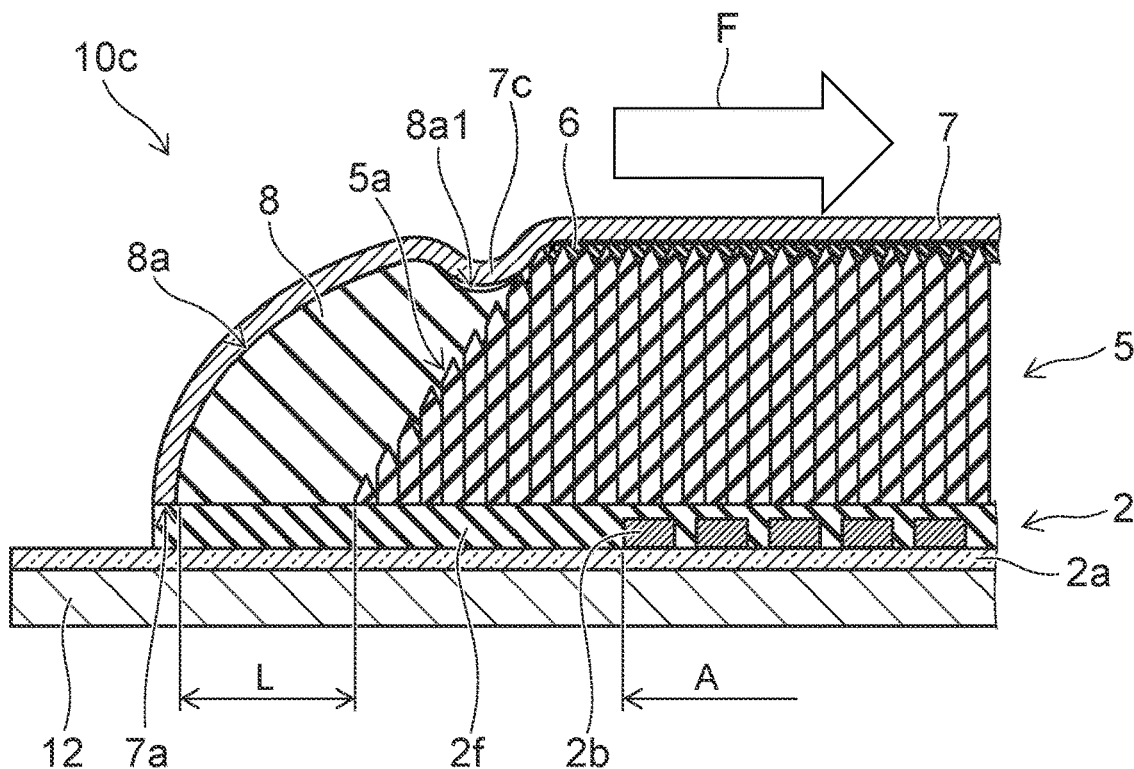
FIG. 7 is a schematic cross-sectional view for illustrating an X-ray detection module according to another embodiment.

FIG. 7 is a schematic cross-sectional view for illustrating an X-ray detection module 10c according to another embodiment.

As described above, the material of the array substrate 2, the material of the scintillator 5, the material of the moisture-resistant part 7, and the material of the sealing part 8 are different. Therefore, each has a different linear expansion coefficient. Here, the temperatures of these materials are high because heat is generated during the startup of the X-ray detection module 10c. There are also cases where the temperature around the X-ray detector 1 changes. Therefore, thermal stress is generated between these materials according to the temperature change. In such a case, when tensile stress F is generated in the moisture-resistant part 7, there is a risk that the tensile stress F may be applied to the bonding portion of the moisture-resistant part 7 and the sealing part 8 or the bonding portion of the sealing part 8 and the array substrate 2; and peeling and rupture, etc., may occur. When peeling and rupture, etc., occur, the moisture easily reaches the scintillator 5. Also, there is a risk that deformation such as warp, etc., may occur in the array substrate 2.

Therefore, in the X-ray detection module 10c according to the embodiment, a recess 8a1 is provided in the outer surface 8a of the sealing part 8. If the recess 8a1 is provided, the vicinity of the recess 8a1 easily deforms. Therefore, the tensile stress F that is generated by the deformation of the vicinity of the recess 8a1 can be relaxed.

Also, a sag portion 7c can be provided at the portion of the moisture-resistant part 7 facing the recess 8a1. The sag portion 7c can undergo elastic deformation more easily than the portion of the moisture-resistant part 7 in which the sag portion 7c is not provided. If the sag portion 7c is provided, the tensile stress F that is generated by the elastic deformation of the sag portion 7c can be relaxed. In such a case, the sag portion 7c and the recess 8a1 may contact each other, or a gap may be provided between the sag portion 7c and the recess 8a1 as shown in FIG. 7. If the sag portion 7c and the recess 8a1 contact each other, the rigidity of the sag portion 7c can be increased; therefore, the occurrence of rupture and/or pinholes in the sag portion 7c can be suppressed. If a gap is provided between the sag portion 7c and the recess 8a1, the deformation of the sag portion 7c is easy; therefore, the relaxation of the tensile stress F is easy.

As long as the tensile stress F can be relaxed, the peeling and rupture, etc., of the moisture-resistant part 7 can be suppressed. Also, the occurrence of deformation such as warp, etc., in the array substrate 2 can be suppressed.

Figure 15:
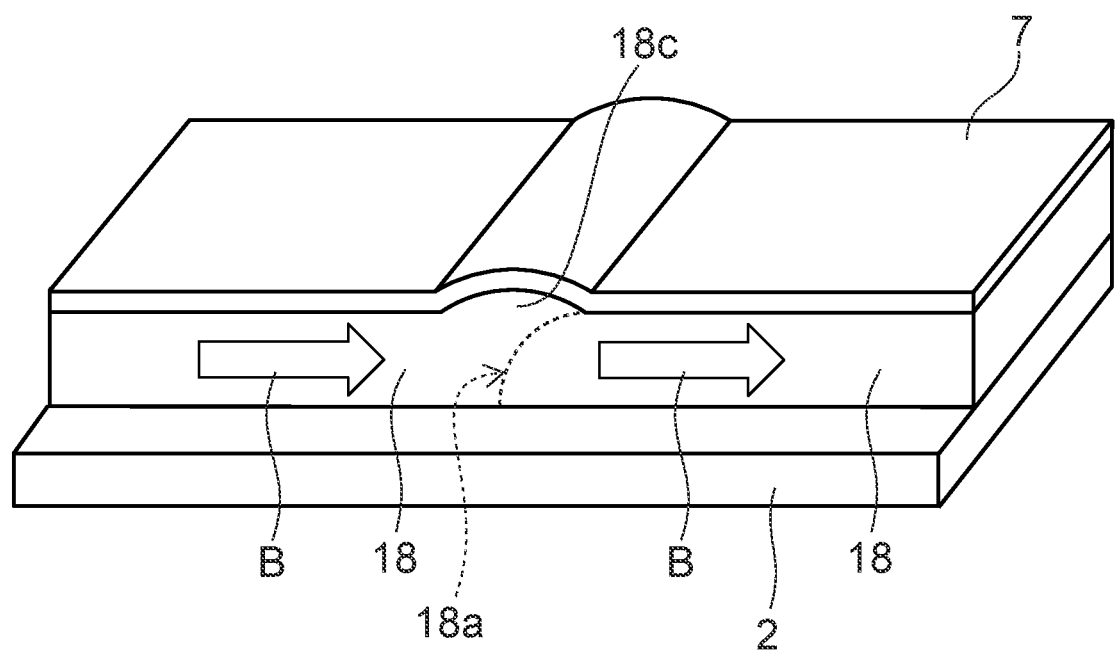
FIG. 15 is a schematic perspective view for illustrating a coating of a thermoplastic resin according to the embodiment.

As shown in FIG. 15 described below, a protrusion 18c also can be provided in the outer surface 8a of the sealing part 8. Details relating to the protrusion 18c are described below.

Figure 8:
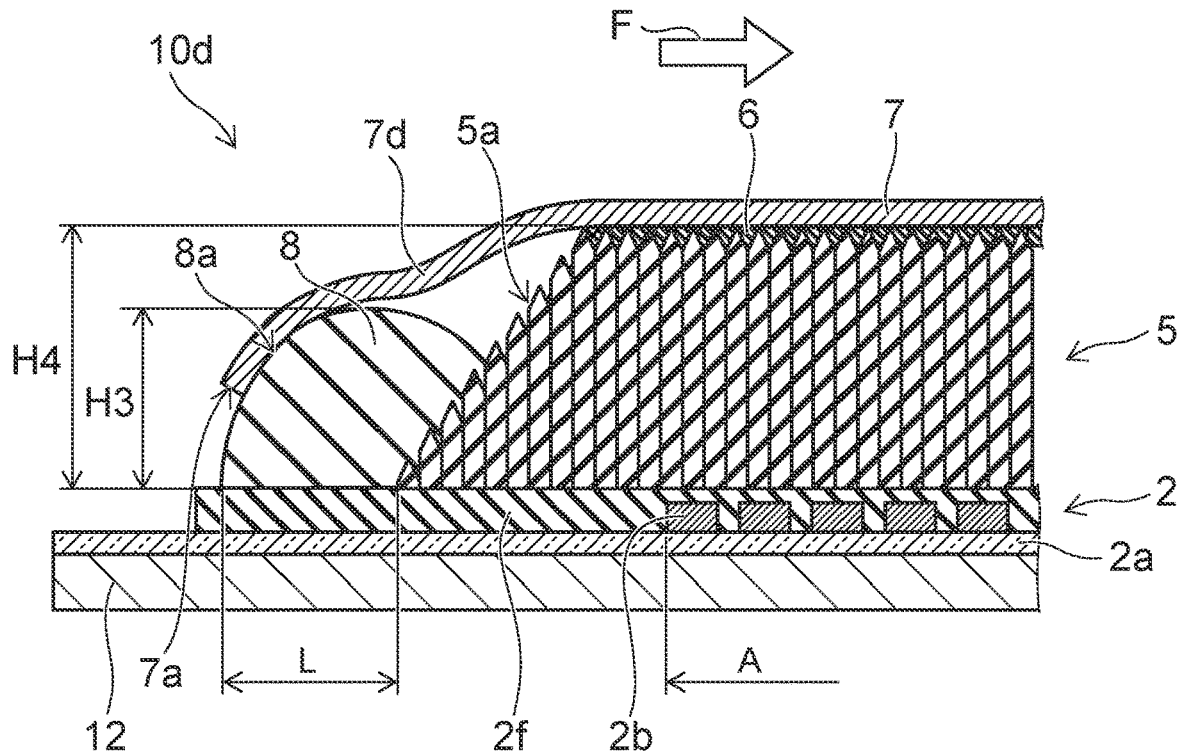
FIG. 8 is a schematic cross-sectional view for illustrating an X-ray detection module according to another embodiment.

FIG. 8 is a schematic cross-sectional view for illustrating an X-ray detection module 10d according to another embodiment.

As shown in FIG. 8, a height H3 of the sealing part 8 can be set to be less than a height H4 of the scintillator 5. If the height H3 of the sealing part 8 is less than the height H4 of the scintillator 5, the peripheral edge vicinity of the moisture-resistant part 7 can sag. In other words, thus, it is easy to provide a sag portion 7d at the peripheral edge vicinity of the moisture-resistant part 7. The sag portion 7d can undergo elastic deformation more easily than the portion of the moisture-resistant part 7 in which the sag portion 7d is not provided. If the sag portion 7d is provided, effects similar to the sag portion 7c described above can be obtained. In other words, the tensile stress F that is generated by the elastic deformation of the sag portion 7d can be relaxed; therefore, the occurrence of the peeling and rupture, etc., of the moisture-resistant part 7 and the occurrence of the deformation such as the warp, etc., in the array substrate 2 can be suppressed.

For example, the linear expansion coefficient of the moisture-resistant part 7 that uses an aluminum foil is about $23 \times 10^{-6}$. The linear expansion coefficient of the array substrate 2 is about $4 \times 10^{-6}$. Therefore, when the temperature of the moisture-resistant part 7 fixed to the sealing part 8 decreases, the moisture-resistant part 7 contracts more than the array substrate 2. In such a case, when the moisture-resistant part has a substantially perfect planar configuration, the contraction amount difference cannot be absorbed; and warp occurs in the array substrate 2. Conversely, if the sag portions 7c and 7d are provided, the contraction amount difference can be absorbed; therefore, the occurrence of the warp in the array substrate 2 can be suppressed.

In such a case, the difference between the height H4 of the scintillator 5 and the height H3 of the sealing part 8 can be set to be not less than the thickness of the moisture-resistant part 7. For example, the difference between the height H4 of the scintillator 5 and the height H3 of the sealing part 8 can be set to be not less than 0.1 mm. On the other hand, when the height H3 of the sealing part 8 is too low, there is a risk that the moisture-resistant part 7 and the array substrate 2 may short when a high voltage of static electricity or the like is applied. Therefore, it is favorable for the difference between the height H4 of the scintillator 5 and the height H3 of the sealing part 8 to be not more than 0.5 mm. In other words, it is favorable for the difference between the height H4 of the scintillator 5 and the height H3 of the sealing part 8 to be not less than 0.1 mm and not more than 0.5 mm.

According to knowledge obtained by the inventors, it is favorable for the height H3 of the sealing part 8 to be not less than 30% and not more than 70% of the height H4 of the scintillator 5. By thus setting the height H3 of the sealing part 8, the suppression of the warp of the array substrate 2 described above, a reduction of the moisture permeation amount per unit time, a reduction of the amount of the material necessary to form the sealing part 8, etc., can be realized.

For example, the reduction effect of the moisture permeation amount per unit time can be considered to be as follows.

The following formula holds, in which the total moisture permeation amount per unit time of the moisture-resistant part 7 and the sealing part 8 is Q, the moisture permeation amount per unit time of the moisture-resistant part 7 is Q7, and the moisture permeation amount per unit time of the sealing part 8 is Q8.

$$Q=Q7+Q8$$

In such a case, Q7 is considered to be substantially constant; therefore, the increase and decrease of Q is substantially determined by the increase and decrease of Q8.

Here, the following formula holds, in which the moisture permeance of the sealing part 8 is P, the moisture permeable cross-sectional area of the sealing part 8 is S (mm$^2$), the moisture permeable width of the sealing part 8 is W, the circumference of the sealing part 8 is L (mm), and the height of the sealing part 8 is H (mm).

$$Q8=P \times S/W=P \times L \times H/W$$

Therefore, if the height H of the sealing part 8 is set to be small, the moisture permeation amount Q8 per unit time of the sealing part 8 can be small, and even the total moisture permeation amount Q per unit time of the moisture-resistant part 7 and the sealing part 8 can be small.

In other words, the reliability of the X-ray detection module 10 can be increased because the improvement of the moisture resistance can be realized.

Figure 9A:
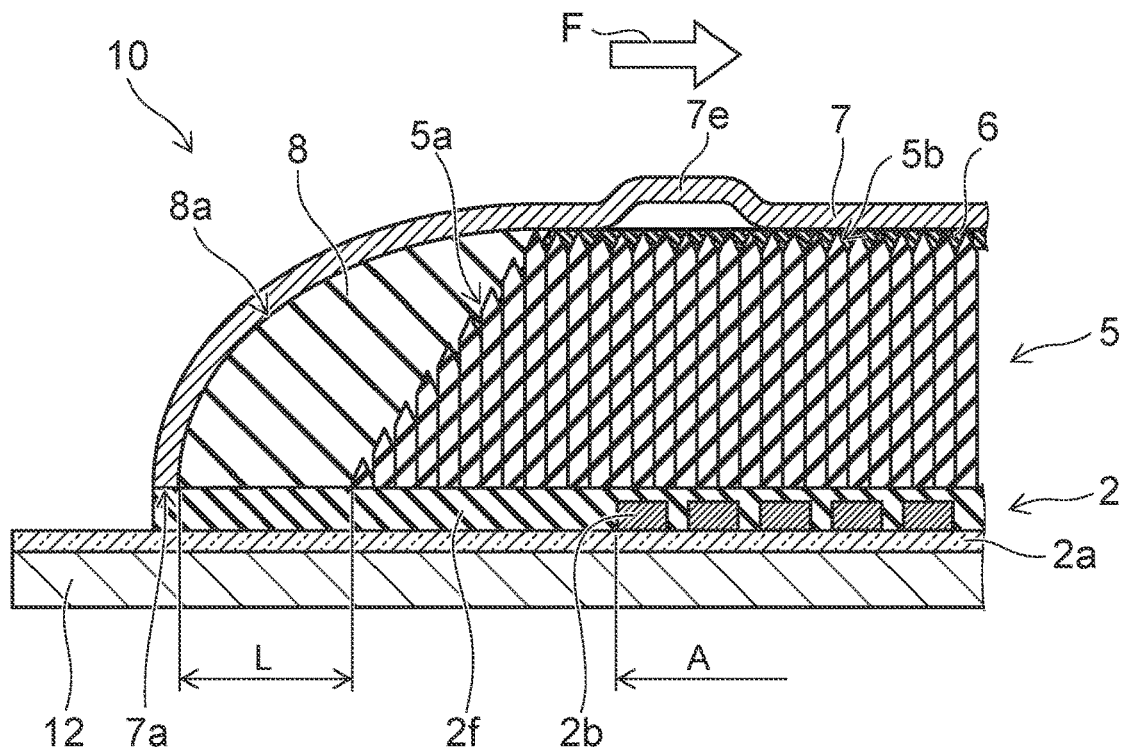
FIGS. 9A and 9B are schematic cross-sectional views for illustrating a sag portion according to another embodiment.
Figure 9B:
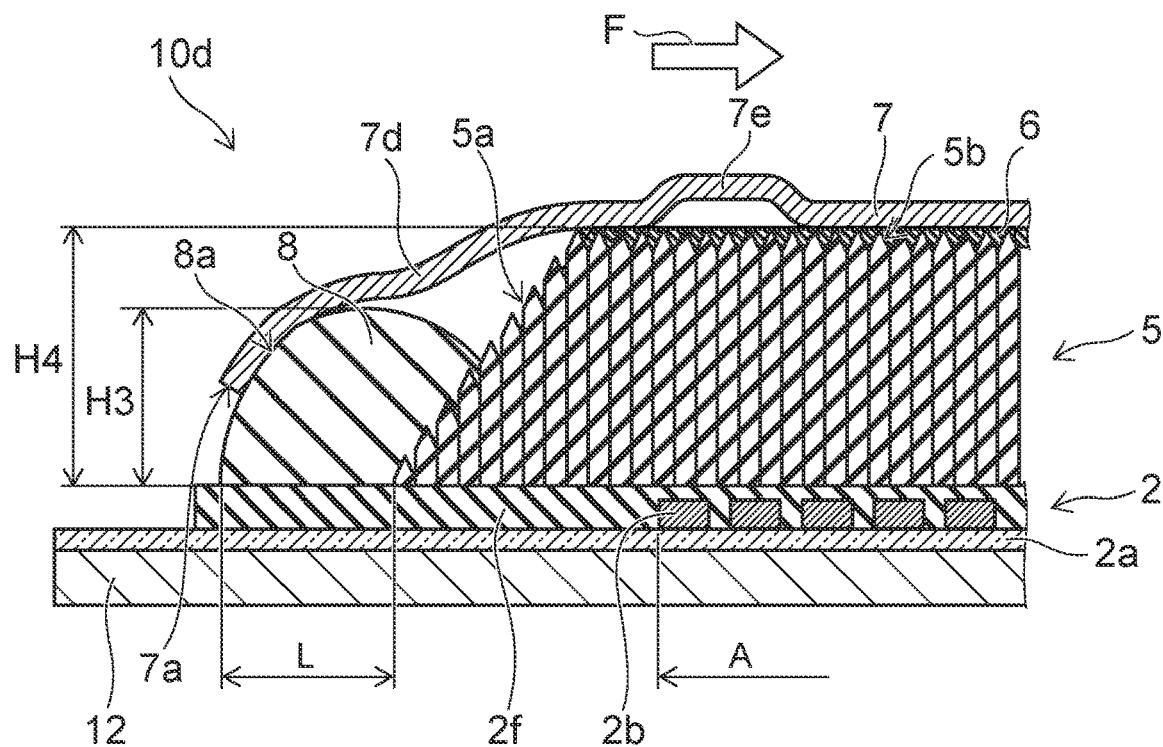

FIGS. 9A and 9B are schematic cross-sectional views for illustrating a sag portion 7e according to another embodiment.

As shown in FIGS. 9A and 9B, the sag portion 7e also can be provided in a region of the moisture-resistant part 7 facing an upper surface 5b of the scintillator 5. For example, the sag portion 7e can have an embossed shape. The surface of the sag portion 7e at the side opposite to the scintillator 5 side (the surface at the side on which the X-rays are incident) protrudes externally from the surface at the side opposite to the scintillator 5 side of the moisture-resistant part 7. The surface of the sag portion 7e at the scintillator 5 protrudes externally from the surface of the moisture-resistant part 7 at the scintillator 5 side.

The wall thickness dimension of the sag portion 7e can be substantially equal to the wall thickness dimension of the portion of the moisture-resistant part 7 in which the sag portion 7e is not provided. For example, the sag portion 7e can be formed by performing stamping (embossing) of the sheet-like moisture-resistant part 7 by a press engraving die. Even in a low-moisture-permeability moisture-resistant film in which a resin film and a film made of an inorganic material are stacked, the sag portion 7e can be formed by performing stamping (embossing) by a press engraving die.

The height dimension of the sag portion 7e can be greater than the wall thickness dimension of the portion of the moisture-resistant part 7 in which the sag portion 7e is not provided. The width dimension, number, arrangement, etc., of the sag portion 7e are not particularly limited. The width dimension, number, arrangement, etc., of the sag portion 7e can be determined as appropriate according to the magnitude of the thermal shrinkage described above, the size of the moisture-resistant part 7, etc.

The sag portion 7e can undergo elastic deformation more easily than the portion of the moisture-resistant part 7 in which the sag portion 7e is not provided. Therefore, the difference of the thermal shrinkage based on the difference of the linear expansion coefficient can be absorbed by the elastic deformation of the sag portion 7e. Therefore, if the sag portion 7e is provided, the occurrence of the warp in the array substrate 2 can be suppressed.

In such a case, only the sag portion 7e can be provided in the moisture-resistant part 7 as shown in FIG. 9A, or the sag portions 7d and 7c also can be provided in the peripheral edge vicinity of the moisture-resistant part 7 in addition to providing the sag portion 7e in the moisture-resistant part 7 as shown in FIG. 9B.

Figure 10:
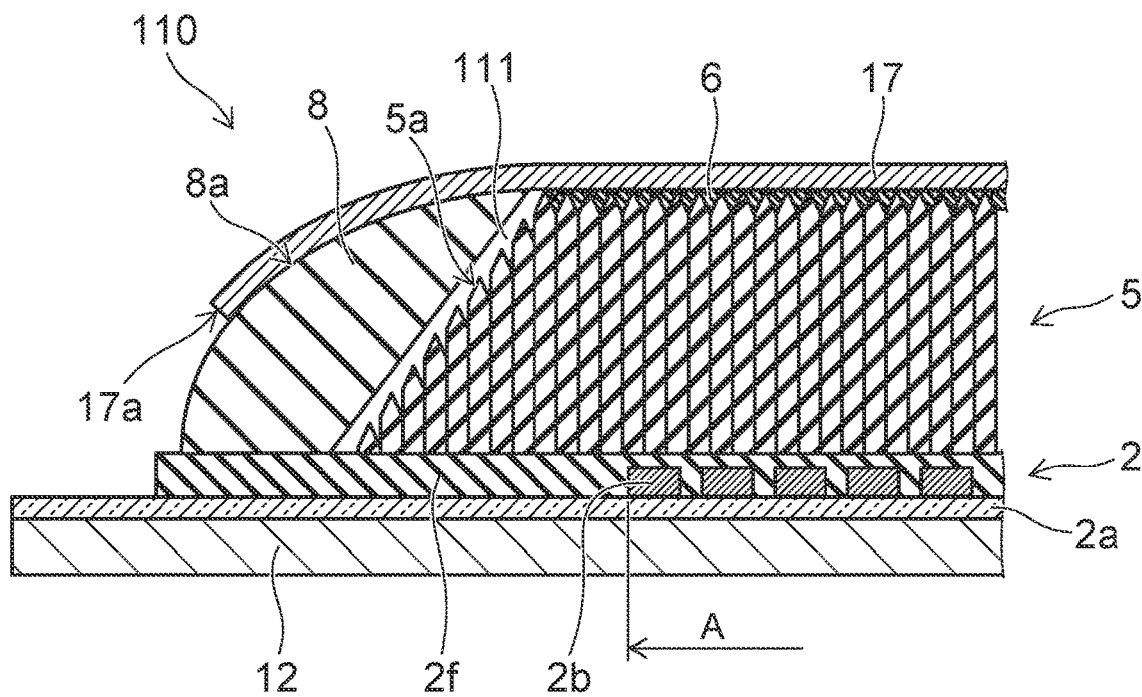
FIG. 10 is a schematic cross-sectional view for illustrating an X-ray detection module according to a comparative example.

FIG. 10 is a schematic cross-sectional view for illustrating an X-ray detection module 110 according to a comparative example. As shown in FIG. 10, if the sealing part 8 is bonded with the array substrate 2 but not bonded with the side surface 5a of the scintillator 5, peeling of the sealing part 8 easily occurs. For example, as described above, thermal stress is generated by the temperature change due to the startup and/or the change of the ambient temperature. In such a case, the bonding strength of the sealing part 8 is low if the sealing part 8 is bonded only with the array substrate 2. Therefore, there is a risk that peeling of the sealing part 8 may occur due to the generated thermal stress.

Conversely, in the X-ray detection modules 10 and 10a to 10c according to the embodiment, the sealing part 8 is bonded to the array substrate 2 and the side surface 5a of the scintillator 5. Also, the sealing part 8 is closely adhered with the side surface 5a of the scintillator 5. Furthermore, a portion of the sealing part 8 is provided inside the unevenness of the side surface 5a of the scintillator 5. Therefore, the bonding strength of the sealing part 8 can be increased; therefore, the peeling of the sealing part 8 due to the thermal stress can be suppressed.

Figure 11:
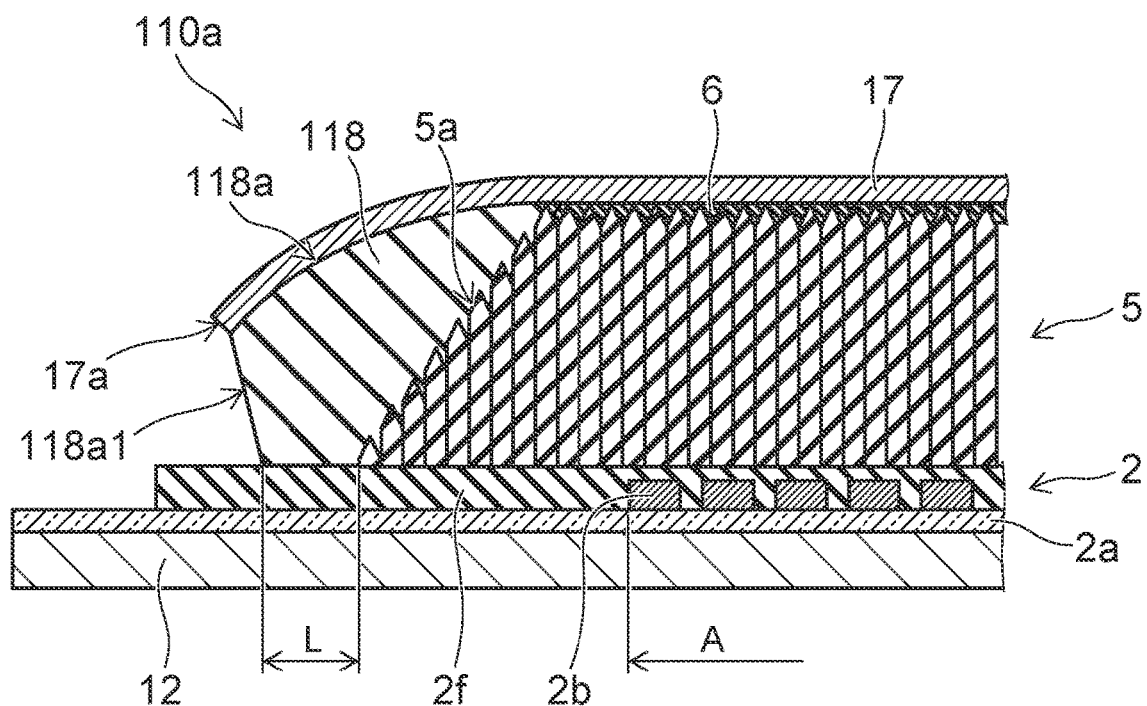
FIG. 11 is a schematic cross-sectional view for illustrating an X-ray detection module according to a comparative example.

FIG. 11 is a schematic cross-sectional view for illustrating an X-ray detection module 110a according to a comparative example.

As shown in FIG. 11, an exposed portion 118a1 of an outer surface 118a of a sealing part 118 is a slanted surface that is slanted in a direction approaching the scintillator 5 toward the array substrate 2 side. Therefore, the distance L between the outer surface 118a of the sealing part 118 and the side surface 5a of the scintillator 5 is short at the vicinity of the array substrate 2. Therefore, the moisture included in ambient air, etc., easily reaches the scintillator 5 by passing between the sealing part 118 and the array substrate 2.

Conversely, in the X-ray detection modules 10 and 10a to 10c according to the embodiment, the shape of the outer surface 8a of the sealing part 8 is a curved surface protruding outward. Therefore, the distance L between the outer surface 8a of the sealing part 8 and the side surface 5a of the scintillator 5 can be increased at the vicinity of the array substrate 2; therefore, it is difficult for the moisture included in ambient air, etc., to reach the scintillator 5.

Figure 12:
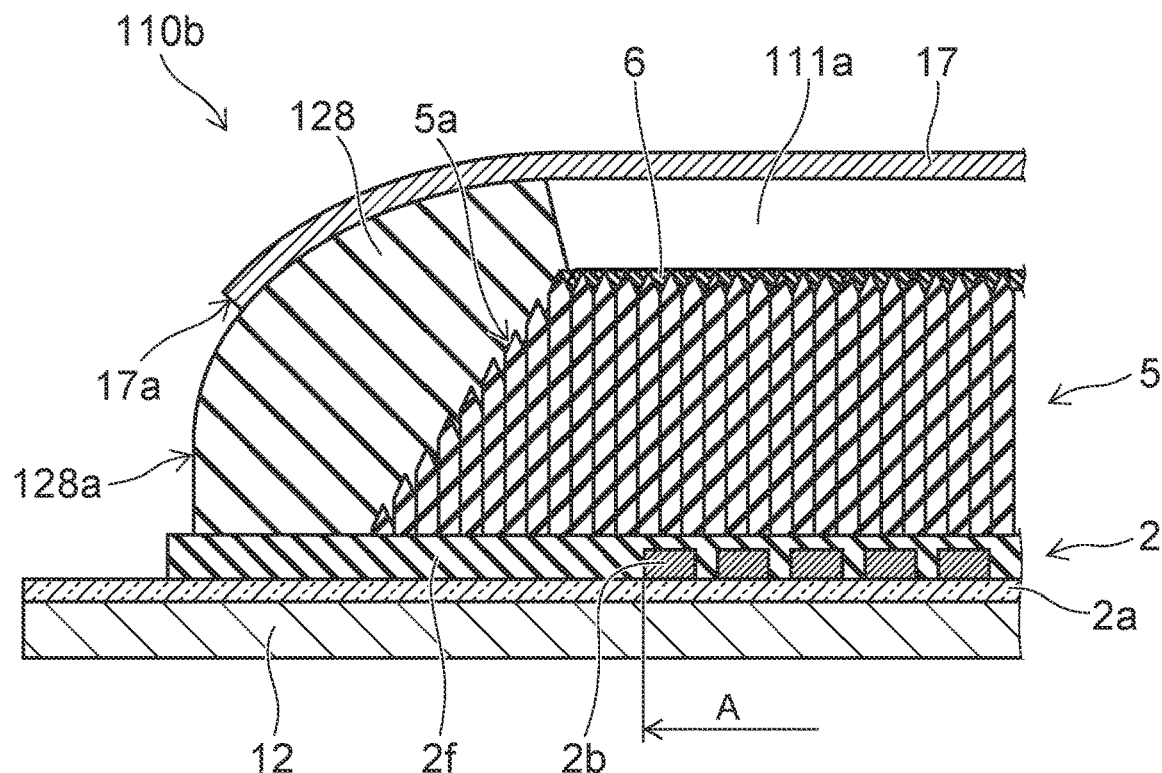
FIG. 12 is a schematic cross-sectional view for illustrating an X-ray detection module according to a comparative example.

FIG. 12 is a schematic cross-sectional view for illustrating an X-ray detection module 110b according to a comparative example.

As shown in FIG. 12, if the height of a sealing part 128 is greater than the height of the scintillator 5, it is necessary to forcibly deform the sheet used to form the moisture-resistant part 17 when covering. Therefore, wrinkles, rupture, pinholes, etc., easily occur in the moisture-resistant part 17.

Also, the exposed portion of an outer surface 128a of the sealing part 128 easily becomes large. When the exposed portion becomes large, the permeation cross section of the moisture becomes large; therefore, more moisture more easily penetrates into the sealing part 128.

Conversely, in the X-ray detection modules 10 and 10a to 10c according to the embodiment, the height of the sealing part 8 is not more than the height of the scintillator 5; therefore, the sheet that is used to form the moisture-resistant part 7 can be deformed without excessive force. Therefore, the occurrence of wrinkles, rupture, pinholes, etc., in the moisture-resistant part 7 can be suppressed.

Figure 13:
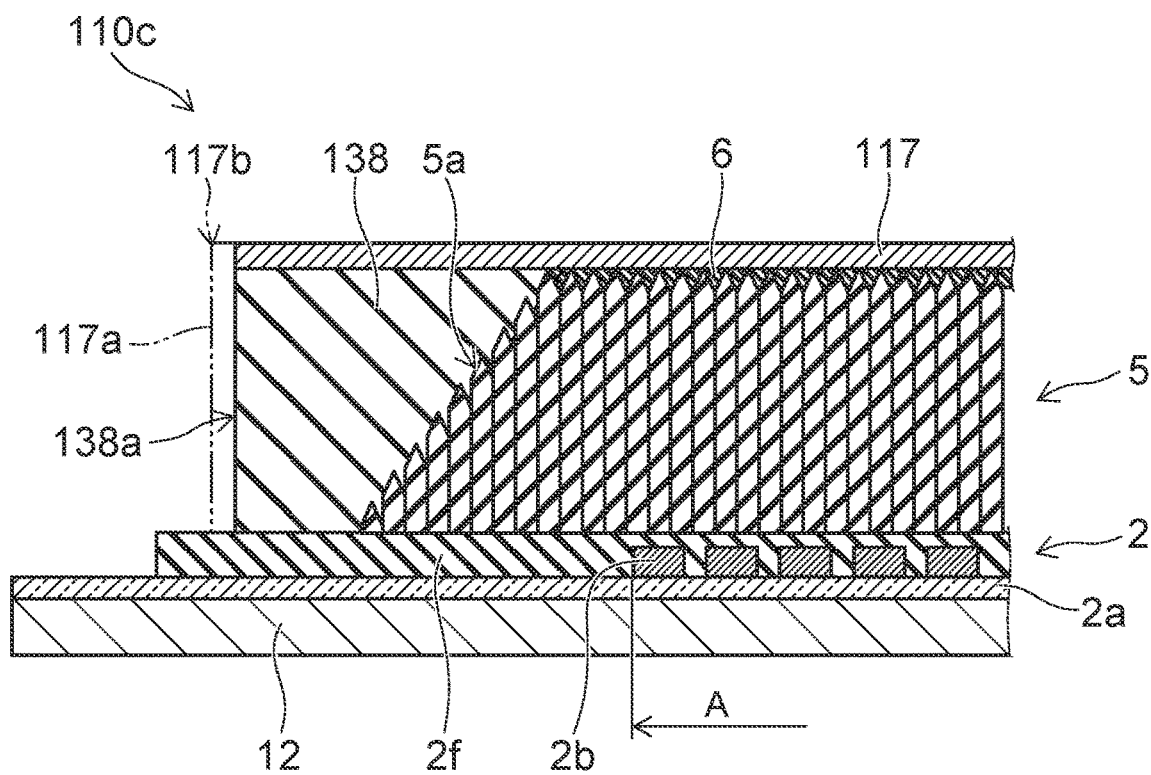
FIG. 13 is a schematic cross-sectional view for illustrating an X-ray detection module according to a comparative example.

FIG. 13 is a schematic cross-sectional view for illustrating an X-ray detection module 110c according to a comparative example.

As shown in FIG. 13, when an outer surface 138a of a sealing part 138 is a plane perpendicular to the array substrate 2, it is difficult to cover the outer surface 138a with a moisture-resistant part 117. When the outer surface 138a is not covered with the moisture-resistant part 117, the permeation cross section of the moisture becomes large; therefore, more moisture more easily penetrates into the sealing part 138. In such a case, when a peripheral edge vicinity 117a of the moisture-resistant part 117 is bent to cover the outer surface 138a, cracks and/or rupture occur easily in a bent portion 117b. When cracks and/or rupture occur, there is a risk that moisture may penetrate via the cracks and/or rupture.

Conversely, in the X-ray detection modules 10 and 10a to 10c according to the embodiment, the shape of the outer surface 8a of the sealing part 8 is a curved surface that protrudes outward. Therefore, when covering the outer surface 8a with the moisture-resistant part 7, a portion at which it is necessary to forcibly bend the moisture-resistant part 7 does not occur. Therefore, the outer surface 8a can be covered with the moisture-resistant part 7 without the occurrence of cracks and/or rupture.

(Method for Manufacturing X-Ray Detection Module and Method for Manufacturing X-Ray Detector)

A method for manufacturing an X-ray detection module and a method for manufacturing an X-ray detector will now be illustrated.

First, the array substrate 2 is manufactured by sequentially forming the control line 2c1, the data line 2c2, the interconnect pad 2d1, the interconnect pad 2d2, the photoelectric converter 2b, the protective layer 2f, etc., on the substrate 2a. For example, the array substrate 2 can be manufactured using a semiconductor manufacturing process. Known technology is applicable to the manufacturing of the array substrate 2, and a detailed description is therefore omitted.

Then, the scintillator 5 is formed to cover the effective pixel region A on the substrate 2a.

For example, the scintillator 5 can be formed using vacuum vapor deposition. If the scintillator 5 is formed using vacuum vapor deposition, the scintillator 5 that is made of an aggregate of multiple columnar crystals is formed. The thickness of the scintillator 5 can be modified as appropriate according to the DQE characteristics, the sensitivity characteristics, the resolution characteristics, etc., that are necessary for the X-ray detector 1. For example, the thickness of the scintillator 5 can be about 600 µm.

Also, a rectangular-prism-shaped scintillator 5 may be provided for each of the multiple photoelectric converters 2*b* by mixing a light-emitting substance and a binder material, coating the mixed material to cover the effective pixel region A, firing the coating, and by forming a trench portion having a matrix configuration in the fired material.

Then, the reflective layer 6 is formed on the scintillator 5.

For example, the reflective layer 6 can be formed by coating, on the scintillator 5, a coating liquid in which a solvent, a resin, and multiple light-scattering particles are mixed, and by drying the coating.

Also, for example, the reflective layer 6 also can be formed by forming, on the scintillator 5, a layer made of a metal having high light reflectance such as a silver alloy, aluminum, etc.

Also, for example, the reflective layer 6 can be provided by providing or adhering, on the scintillator 5, a sheet having a surface made of a metal having high light reflectance such as a silver alloy, aluminum, and the like, a resin sheet including light-scattering particles, etc.

Then, the sealing part 8 is formed.

For example, the sealing part 8 can be formed by softening a thermoplastic resin by using a solvent, coating the softened thermoplastic resin in a frame shape around the scintillator 5, and by curing the thermoplastic resin by evaporating the solvent.

Also, for example, the sealing part 8 can be formed by softening the thermoplastic resin by heating, coating the softened thermoplastic resin in a frame shape around the scintillator 5, and by curing the thermoplastic resin by heat dissipation, etc.

Also, for example, the sealing part 8 that has a frame shape also can be formed by using a 3D printer, etc.

Figure 14:
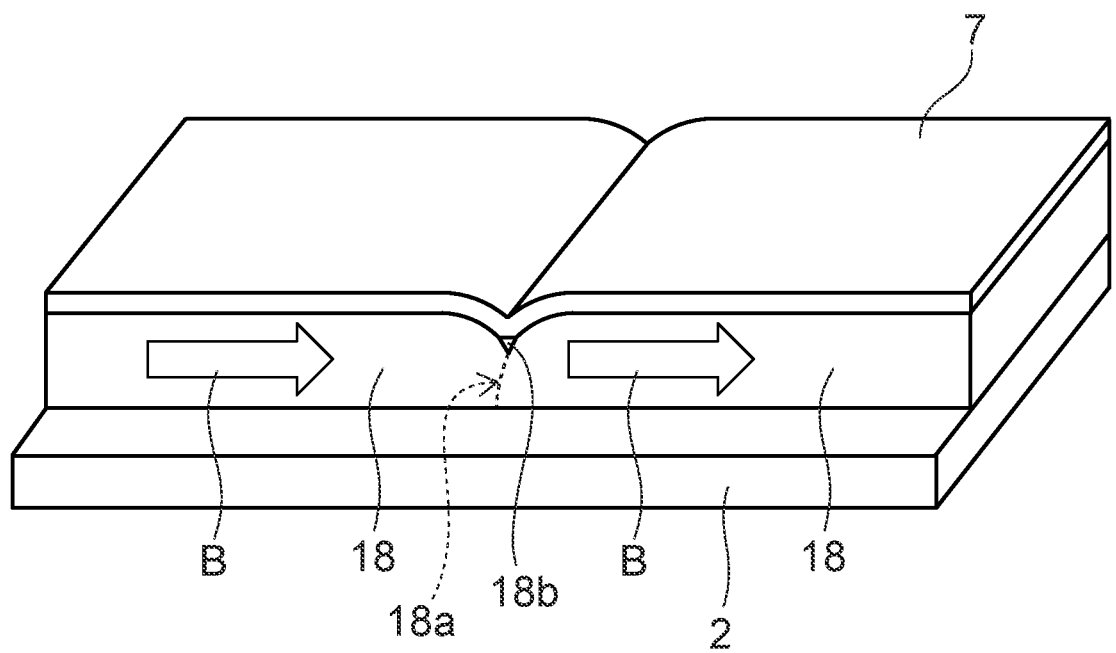
FIG. 14 is a schematic perspective view for illustrating a coating of a thermoplastic resin according to a comparative example.

FIG. 14 is a schematic perspective view for illustrating the coating of the thermoplastic resin 18 according to a comparative example. As described above, the softened thermoplastic resin 18 is coated in a frame shape. Therefore, a joint 18*a* occurs in at least one location. When the softened thermoplastic resin 18 is coated in the frame shape, if the supply amount per unit time of the thermoplastic resin 18 is set to be constant or a movement speed B of the nozzle dispensing the thermoplastic resin 18 is set to be constant, there are cases where a recess 18*b* occurs at the joint 18*a* of the start point of the supply and the end point of the supply as shown in FIG. 14. For example, when the start point of the supply and the end point of the supply are separated, there are cases where a steep recess 18*b* that is lower than the periphery occurs in the joint 18*a* of the start point of the supply and the end point of the supply. When the steep recess 18*b* occurs, there is a risk that the sheet that is used to form the moisture-resistant part 7 cannot be along the recess 18*b*, and a leakage path may occur. The moisture-resistant part 7 and the outer surface 8*a* of the sealing part 8 are not bonded at the leakage path portion; and moisture easily penetrates via the leakage path.

FIG. 15 is a schematic perspective view for illustrating the coating of the thermoplastic resin 18 according to the embodiment.

As shown in FIG. 15, the protrusion 18*c* can be formed in the joint 18*a*. For example, the protrusion 18*c* can be formed at the portion of the joint 18*a* by increasing the supply amount per unit time of the thermoplastic resin 18 or by slowing the movement speed B of the nozzle. In such a case, it is favorable for the protrusion 18*c* to be formed to have a smooth outer surface and to have a low height.

Compared to the steep recess 18*b*, it is easy for the sheet that is used to form the moisture-resistant part 7 to be along the protrusion 18*c*. Therefore, the occurrence of the leakage path can be suppressed.

Then, the sheet that is used to form the moisture-resistant part 7 covers the scintillator 5, the reflective layer 6, and the sealing part 8; and the peripheral edge vicinity of the sheet is bonded to the outer surface 8*a* of the sealing part 8.

For example, the moisture-resistant part 7 can be bonded by causing the outer surface 8*a* of the sealing part 8 to melt by heating the sheet in a state in which the peripheral edge vicinity of the sheet is pressed onto the outer surface 8*a* of the sealing part 8. The moisture-resistant part 7 is formed by bonding the sheet to the outer surface 8*a* of the sealing part 8.

The bonding of the sheet can be performed in an environment depressurized from atmospheric pressure.

The sheet is bonded to the outer surface 8*a* of the sealing part 8 in an environment depressurized from atmospheric pressure. The storage of air including water vapor inside the moisture-resistant part 7 can be suppressed thereby. Also, even when the X-ray detector 1 is located in an environment depressurized from atmospheric pressure such as when the X-ray detector 1 is transported by an aircraft, etc., the expansion and the deformation of the moisture-resistant part 7 due to the air inside the moisture-resistant part 7 can be suppressed. Also, the moisture-resistant part 7 is closely adhered to the scintillator 5 because the moisture-resistant part 7 is pressed by atmospheric pressure.

Thus, the X-ray detection modules 10 and 10*a* to 10*c* can be manufactured.

Then, the array substrate 2 and the circuit board 11 are electrically connected via the flexible printed circuit boards 2*e*1 and 2*e*2.

Other circuit components, etc., are mounted as appropriate.

Then, the array substrate 2, the circuit board 11, etc., are housed inside a not-illustrated housing.

In such a case, when the warp of the array substrate 2 is large, there is a risk that the array substrate 2 may interfere with members housed inside the housing, or the array substrate 2 may interfere with the interior wall of the housing. As described above, in the X-ray detection module 10 according to the embodiment, the warp of the array substrate 2 can be suppressed; therefore, smooth operations in the assembly process can be realized.

Also, an X-ray image test, an electrical test that checks the existence or absence of an abnormality of the photoelectric conversion element 2*b*1 and/or the existence or absence of an abnormality of the electrical connection, etc., can be performed as necessary.

Thus, the X-ray detector 1 can be manufactured.

A high-temperature high-humidity test, a temperature cycle test, etc., also can be performed to check the moisture resistance reliability of the product and/or the reliability with respect to the change of the thermal environment.

As described above, the method for manufacturing the X-ray detection module according to the embodiment can include the following processes:

A process of forming the scintillator 5 on the multiple photoelectric converters 2*b* provided in the array substrate 2.

A process of forming the sealing part 8 by coating the softened thermoplastic resin 18 in a frame shape around the scintillator 5.

A process of covering the scintillator 5 and the sealing part 8 with a sheet used to form the moisture-resistant part 7, and bonding the peripheral edge vicinity of the sheet to the outer surface 8a of the sealing part 8 by heating the peripheral edge vicinity of the sheet.

In such a case, the protrusion 18c can be formed at the joint 18a of the coating in the process of forming the sealing part 8.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions. Moreover, above-mentioned embodiments can be combined mutually and can be carried out.

What is claimed is:

1. A radiation detection module, comprising:
    an array substrate including a plurality of photoelectric converters;
    a scintillator provided on the plurality of photoelectric converters;
    a sealing part provided around the scintillator and bonded to the array substrate and the scintillator, the sealing part including a thermoplastic resin as a major component, the sealing part having a frame shape, a shape of an outer surface on an outer peripheral side of the sealing part being a curved surface protruding outward; and
    a moisture-resistant part covering the scintillator and the outward-protruding surface of the sealing part from above, and a peripheral edge vicinity of the moisture-resistant part being bonded to the outward-protruding curved surface of the sealing part.

2. The radiation detection module according to claim 1, wherein a peripheral end surface of the moisture-resistant part contacts the array substrate.

3. The radiation detection module according to claim 1, wherein a peripheral end surface of the moisture-resistant part is provided at a vicinity of the array substrate.

4. The radiation detection module according to claim 1, wherein a distance between the array substrate and a peripheral end surface of the moisture-resistant part is not more than one-half of a height of the sealing part.

5. The radiation detection module according to claim 1, wherein a bent portion that is along the array substrate is provided in the peripheral edge of the moisture-resistant part.

6. The radiation detection module according to claim 5, wherein a protrusion that protrudes outward is provided at a corner portion of the moisture-resistant part.

7. The radiation detection module according to claim 1, wherein a recess is provided in the outward-protruding curved surface of the sealing pail.

8. The radiation detection module according to claim 7, wherein a sag portion is provided in a portion of the moisture-resistant part facing the recess.

9. The radiation detection module according to claim 1, wherein a protrusion is provided at the outward protruding curved surface of the sealing part.

10. The radiation detection module according to claim 1, wherein a maximum height of the sealing part from a top surface of the array substrate is not more than a maximum height of the scintillator from the top surface of the array substrate.

11. The radiation detection module according to claim 10, wherein a difference between the maximum height of the scintillator and the maximum height of the sealing part is not less than 0.1 mm and not more than 0.5 mm.

12. The radiation detection module according to claim 10, wherein the maximum height of the sealing part is not less than 30% and not more than 70% of the maximum height of the scintillator.

13. The radiation detection module according to claim 1, wherein
    air unevenness is provided in a side surface of the scintillator, and
    a portion of the sealing part is provided inside the unevenness of the side surface of the scintillator.

14. The radiation detection module according to claim 1, wherein the sealing part is transmissive.

15. The radiation detection module according to claim 1, wherein at least the outward-protruding curved surface of the sealing part is water-repellent.

16. The radiation detection module according to claim 1, wherein the thermoplastic resin is at least one of polyethylene or polypropylene.

17. The radiation detection module according to claim 1, wherein the thermoplastic resin further includes a filler including an inorganic material.

18. The radiation detection module according to claim 1, wherein the moisture-resistant part is a sheet including a metal, a stacked sheet in which a resin film and a metal film are stacked, or a stacked sheet in which a resin film and an inorganic film are stacked.

19. The radiation detection module according to claim 1, wherein a thickness of the moisture-resistant part is not less than 10 μm and not more than 50 μm.

20. The radiation detection module according to claim 1, wherein
    the moisture-resistant part includes a sag portion, and
    the sag portion undergoes elastic deformation more easily than a portion of the moisture-resistant part in which the sag portion is not provided.

21. The radiation detection module according to claim 1, wherein a rigidity of the thermoplastic resin is less than a rigidity of the moisture-resistant part.

22. The radiation detection module according to claim 1, wherein a pressure of a space defined by the sealing part and the moisture-resistant part is less than atmospheric pressure.

23. The radiation detection module according to claim 1, wherein the scintillator includes cesium iodide (CsI):thallium (Tl).

24. The radiation detection module according to claim 1, further comprising:
    a reflective layer provided between the scintillator and the moisture-resistant part.

25. A radiation detector, comprising:
    the radiation detection module according to claim 1; and
    a circuit board electrically connected with the radiation detection module.

26. A method for manufacturing a radiation detection module, the method comprising:

forming a scintillator on a plurality of photoelectric converters provided in an array substrate;
forming a sealing part by coating a softened thermoplastic resin in a frame shape around the scintillator; and
covering the scintillator and the sealing part with a sheet used to form a moisture-resistant part, and bonding a peripheral edge vicinity of the sheet to an outer surface of the sealing part by heating the peripheral edge vicinity of the sheet,
wherein the forming of the sealing part includes forming a protrusion at a joint between a start position and an end position of the frame-shaped coating.

* * * * *